(12) United States Patent
Era

(10) Patent No.: US 9,523,674 B2
(45) Date of Patent: Dec. 20, 2016

(54) METHOD OF SCREENING FOR SUBSTANCES CAPABLE OF PROMOTING INDUCTION OF INDUCED PLURIPOTENT STEM CELLS

(75) Inventor: Takumi Era, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 14/343,533

(22) PCT Filed: Sep. 12, 2012

(86) PCT No.: PCT/JP2012/073272
§ 371 (c)(1),
(2), (4) Date: Jul. 24, 2014

(87) PCT Pub. No.: WO2013/039087
PCT Pub. Date: Mar. 21, 2013

(65) Prior Publication Data
US 2015/0160194 A1    Jun. 11, 2015

(30) Foreign Application Priority Data
Sep. 12, 2011 (JP) .................... 2011-197931

(51) Int. Cl.
G01N 33/50 (2006.01)
C12N 5/074 (2010.01)

(52) U.S. Cl.
CPC ......... *G01N 33/5023* (2013.01); *C12N 5/0696* (2013.01); *G01N 33/5073* (2013.01); *C12N 2501/999* (2013.01); *C12N 2503/02* (2013.01); *C12N 2506/09* (2013.01); *C12N 2510/00* (2013.01); *G01N 2500/10* (2013.01)

(58) Field of Classification Search
CPC G01N 33/502; G01N 33/5073; C12N 5/0696; C12N 2509/09
See application file for complete search history.

(56) References Cited

FOREIGN PATENT DOCUMENTS

WO    2007/069666    6/2007

OTHER PUBLICATIONS

Ho, Thach-Vu, et al. "Current Status of Induced Pluripotent Stem Cells." Tissue Engineering in Regenerative Medicine. Humana Press, Jul. 2011. 39-52.*
Carvajal-Vergara et al. Patient-specific induced pluripotent stem-cell-derived models of LEOPARD syndrome. Nature, vol. 465, pp. 808-814, Jun. 2010.*
Hamasaki et al. Pathogenic mutation of ALK2 inhibits induced pluripotent stem cell reprogramming and maintenance: Mechanisms of reprogramming and strategy for drug identification. Stem Cells, vol. 30, pp. 2437-2449, Sep. 4, 2012.*
Mali et al. Butyrate greatly enhances derivation of human induced pluripotent stem cells by promoting epitgenetic remodeling and the expression of pluripotency-associated genes. Stem Cells, vol. 28, pp. 713-720, Mar. 2010, including pp. 1/22-2/22 of Supplemental materials.*
Hsiao et al. Modeling skeletal diseases in iPS cells. Journal of Bone and Mineral Research, vol. 26, Supplement 1, Abstract No. 1183, Meeting Info: 2011 Annual Meeting of the American Society for Bone and Mineral Research, ASBMR 2011. San Diego, CA, United States. Sep. 16, 2011-Sep. 20, 2011.*
Yamanaka, S. Patient-specific pluripotent stem cells become even more accessible. Cell Stem Cell, vol. 7, pp. 1-2, Jul. 2010.*
Fusaki, "Sendai Virus Vector o Mochiita Idenshi Sonyu no Nai Shikkan Yurai iPS Saibokabu no Juritsu ni Kansuru Kenkyu", Buntan Kenkyu Hokokusho, Mar. 2011, pp. 27-31.
Shafritz et al., "Overexpression of an Osteogenic Morphogen in Fibrodysplasia Ossificans Progressiva", N Engl J Med 335, 1996, pp. 555-561.
Soldner et al., "Parkinson's Disease Patient-Derived Induced Pluripotent Stem Cells Free of Viral Reprogramming Factors", Cell 136, 2009, pp. 964-977.
Kaplan et al., "Classic and Atypical Fibrodysplasia Ossificans Progressiva (FOP) Phenotypes Are Caused by Mutations in the Bone Morphogenetic Protein (BMP) Type I Receptor ACVR1", Hum Mutat 30, 2009, pp. 379-390.
Niwa et al., "Interaction between Oct3/4 and Cdx2 Determines Trophectoderm Differentiation", Cell 123, 2005, pp. 917-929.
Fukuda et al., "A unique mutation of ALK2, G356D, found in patient with fibrodysplasia ossificans progressiva is a moderately activated BMP type I receptor", Biochem Biophys Res Commun 377, 2008, pp. 905-909.
Billings et al., "Dysregulated BMP Signaling and Enhanced Osteogenic Differentiation of Connective Tissue Progenitor Cells From Patients With Fibrodysplasia Ossificans Progressiva (FOP)", J Bone Miner Res 23, 2008, pp. 305-313.
Sakurai et al., "In Vitro Modeling of Paraxial and Lateral Mesoderm Differentiation Reveals Early Reversibility", Stem Cells 24, 2006, pp. 575-586.
Kaplan et al., "Investigations of Activated ACVR1/ALK2, A Bone Morphogenetic Protein Type I Receptor, That Causes Fibrodysplasia Ossificans Progressiva", Methods Enzymol 484, 2010, pp. 357-373.

(Continued)

*Primary Examiner* — Jennifer Dunston
(74) *Attorney, Agent, or Firm* — Greenblum & Bernstein, P.L.C.

(57) ABSTRACT

The object of the present invention is to provide a method for screening a substance capable of promoting induction of induced pluripotent stem cells from cells derived from an individual affected by a disease for which it is impossible to produce induced pluripotent stem cells simply by introducing reprogramming genes. The present invention provides a method for screening a substance, which comprises culturing cells derived from an individual affected by a disease for which it is impossible to produce induced pluripotent stem cells simply by introducing reprogramming genes, the cells being transfected with reprogramming genes, in the presence of test substances, and selecting a test substance capable of promoting induction of induced pluripotent stem cells from the cells.

8 Claims, 7 Drawing Sheets

(56) References Cited

OTHER PUBLICATIONS

Toguchida, "Nanchisei Kotsu Nankotsu Shikkan Tokuiteki iPS Saibo Sakusei to Byotai Kaimei", Buntan Kenkyu Hokokusho, Mar. 2011, pp. 17-18.

Marchetto et al., "A Model for Neural Development and Treatment of Rett Syndrome Using Human Induced Pluripoten Stem Cells", Cell 143, 2010, pp. 527-539.

Era et al., "Nanchisei Shikkan Yurai Gairai Inshi Free Jinko Tanosei Kansaibo no Itaku Sakusei to Bank-ka ni Kansuru Kenkyu", Buntan Kenkyu Hokokusho, Mar. 2011, pp. 4-12.

Furuya et al., "A Unique Case of Fibrodysplasia Ossificans Progressiva With an ACVR1 Mutation, G356D, Other Than the Common Mutation (R206H)", Am J Med Genet A 146A, 2008, pp. 459-463.

Shore et al., "A recurrent mutation in the BMP type I receptor ACVR1 causes inherited and sporadic fibrodysplasia ossificans progressiva", Nat Genet 38, 2006, pp. 525-527.

Dimos et al., "Induced Pluripotent Stem Cells Generated from Patients with ALS Can Be Differentiated into Motor Neurons", Science 321, 2008, pp. 1218-1221.

Yu et al., "BMP type I receptor inhibition reduces heterotopic ossification", Nat Med. 14, 2008, pp. 1-14.

Tada et al., "Characterization of mesendoderm: a diverging point of the definitive endoderm and mesoderm in embryonic stem cell differentiation culture", Development 132, 2005, pp. 4363-4374.

Liu et al., "Recapitulation of premature ageing with iPSCs from Hutchinson-Gilford progeria syndrome", Nature 472, 2011, pp. 221-227.

Mitsui et al., "The Homeoprotein Nanog Is Required for Maintenance of Pluripotency in Mouse Epiblast and ES Cells", Cell 113, 2003, pp. 631-642.

Ebert et al., "Induced pluripotent stem cells from a spinal muscular atrophy patient", Nature 457, 2009, pp. 277-281.

Fusaki et al., "Efficient induction of transgene-free human pluripoten stem cells using a vector based on Sendai virus, an RNA virus that does not integrate into the host genome" Proc. Jpn. Acad., Ser. B85, 2009, pp. 348-362.

Niwa et al., "Quantitative expression of Oct-3/4 defines differentiation, dedifferentiation or self-renewal of ES cells", Nat Genet 24, 2000, pp. 372-376.

Shore et al., "Insights from a Rare Genetic Disorder of Extra-Skeletal Bone Formation, Fibrodysplasia Ossificans Progressiva", Bone 43, 2008, pp. 1-16.

Fukuda et al., "Constitutively Activated ALK2 and Increased SMAD1/5 Cooperatively Induce Bone Morphogenetic Protein Signaling in Fibrodysplasia Ossificans Progressiva", J Biol Chem. 284, 2009, pp. 7149-7156.

Chambers et al., "Functional Expression Cloning of Nanog, a Pluripotency Sustaining Factor in Embryonic Stem Cells", Cell 113, 2003, pp. 643-655.

Fiori et al., "Dysregulation of the BMP-p38 MAPK Signaling Pathway in Cells From Patients with Fibrodysplasia Ossificans Progressiva (FOP)", J Bone Miner Res 21, 2006, pp. 902-909.

Cuny et al., "Structure-activity relationship study of bone morphogenetic protein (BMP) signaling inhibitors", Bioorg Med Chem Lett 18, 2008, pp. 4388-4392.

Takashima et al., "Neuroepithelial Cells Supply an Initial Transient Wave of MSC Differentiation", Cell 129, 2007, pp. 1377-1388.

Shen et al., "The fibrodysplasia ossificans progressiva R206H ACVR1 mutation activates BMP-independent chondrogenesis and zebrafish embryo ventralization", J Clin Invest 119, 2009, pp. 3462-3472.

Katsuno et al., "Bone morphogenetic protein signaling enhances invasion and bone metastasis of breast cancer cells through Smad pathway", Oncogene, 27, 2008, pp. 6322-6333.

International Search Report for PCT/JP2012/073272, mailed Dec. 18, 2012, along with an English language translation.

International Preliminary Report on Patentability for PCT/JP2012/073272, mailed Mar. 20, 2014, along with an English language translation.

* cited by examiner

Fig. 1
A
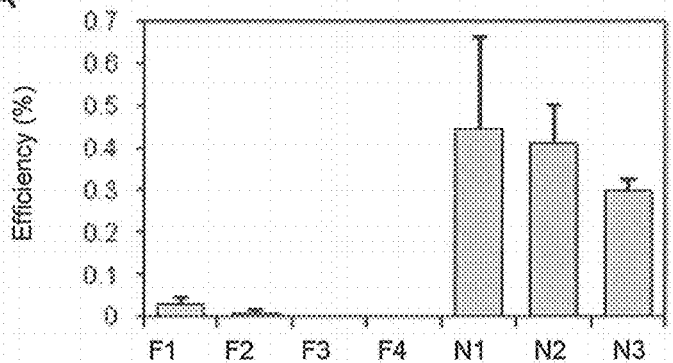
B
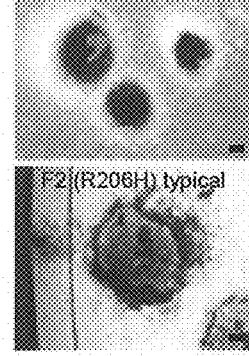
C
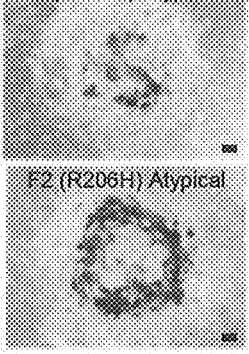
D
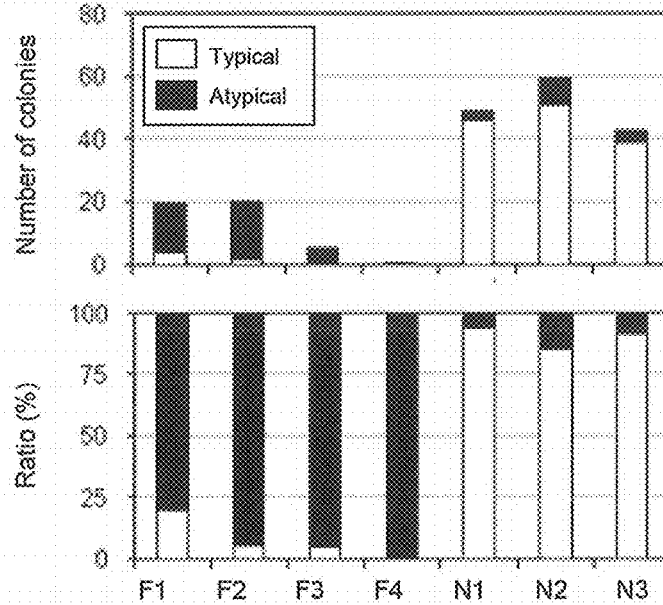

Fig. 4
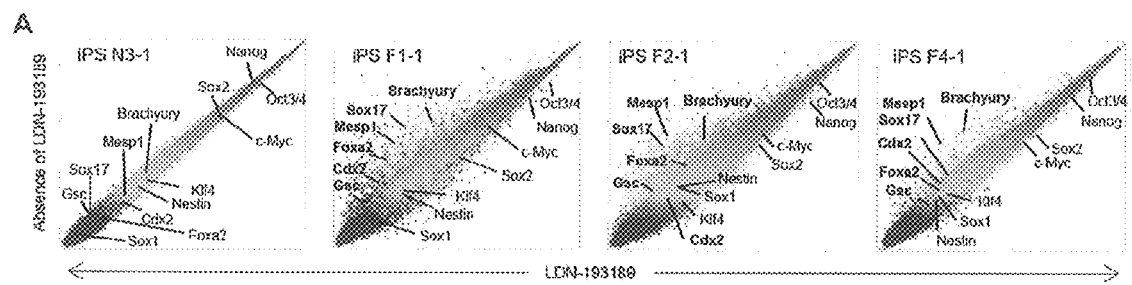
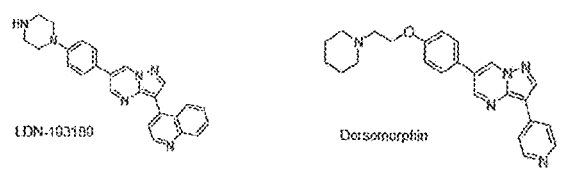

| NaB treatment | — | + |
|---|---|---|
| Number of AP-positive iPS cell colonies | 0 | 562 |
| Induction efficiency | 0% | 0.16% |

… # METHOD OF SCREENING FOR SUBSTANCES CAPABLE OF PROMOTING INDUCTION OF INDUCED PLURIPOTENT STEM CELLS

SEQUENCE LISTING

The instant application contains a Sequence Listing which has been submitted electronically in ASCII format and is hereby incorporated by reference in its entirety. Said ASCII copy, created on Nov. 13, 2015, is named P45376_SL.txt and is 25,458 bytes in size.

TECHNICAL FIELD

The present invention relates to a method for screening a substance capable of promoting induction of induced pluripotent stem cells from cells derived from individuals affected by a disease for which it is impossible to produce induced pluripotent stem cells simply by introducing reprogramming genes.

BACKGROUND ART

Fibrodysplasia ossificans progressiva (FOP) is a congenital and progressive disorder that cause a wide range of ossification of soft tissue and/or muscle after birth (Non-Patent Documents 1-3). Main symptoms of the disease are severe weakness, decreased life expectancy due to joint adhesion, and restrictive ventilatory impairment associated with the thoracic region. The respiratory function in FOP patients is gradually impaired, eventually causing death at about 40 years old due to respiratory failure. There is no effective treatment for preventing FOP-related ectopic ossification. The recent studies revealed that mutation of activin A receptor 1 (ACVR1) known as BMP type I receptor ALK2 causes the disease (Non-Patent Documents 3-9). One of the most common mutations of ALK2 is R206H which is considered to cause a change in kinase activity of ALK2, thereby inducing a constitutive increase in kinase activity of ALK2. For example, some other mutations of ALK2 such as G356D have been reported in the case of phenotypic variation of FOP. It is reported that such mutations also affect kinase activity so as to cause constitutive activation of ALK2 (Non-Patent Document 10). Therefore, it has been shown that kinase activity of ALK2 (G356D) is weaker than that of ALK2 (R206H), suggesting that such clinical change is derived from differences in bioactivity of ALK2 mutants (Non-Patent Document 11).

In addition, diseases caused by decreased functions of mitochondria are collectively referred to as "mitochondrial diseases." Typical mitochondrial diseases are chronic progressive external ophthalmoplegia (CPEO), myoclonus epilepsy associated with ragged-red fibers (MERRF), and mitochondrial encephalomyopathy, lactic acidosis, stroke-like episodes (MELAS). The mitochondrial diseases show a variety of morphological conditions because mitochondria do not uniformly cause abnormalities in all in vivo cells, and therefore, the diseases are intractable diseases for which there is no fundamental treatment.

Further, lysosomal diseases are caused by deletion of enzymes associated with lysosome which is an organelle. The diseases cause in vivo accumulation of substances that should be disintegrated under normal conditions. Lysosomal diseases have different names and symptoms depending on the types of deleted enzymes. At present, there exist about 30 types of lysosomal diseases. Currently available methods for treating lysosomal diseases include enzyme replacement therapy, organ transplantation, and bone-marrow transplantation. However, such methods provide substantially no effect on some symptoms. There is no known fundamental treatment.

Meanwhile, induced pluripotent stem cells (iPS cells) derived from somatic cells of patients are expected to be used as potential tools not only for biomedical studies but also for investigation of effects of drugs acting on cells derived from patients. It has been revealed that iPS cells generated from cells affected by a specific disease can reproduce phenotypes related to the disease. However, it is still unknown how disease-specific pathogenicity influences generation and maintenance of human iPS cells. There is no known example demonstrating that iPS cells can be produced for intractable diseases such as fibrodysplasia ossificans progressiva, mitochondrial diseases, and lysosomal diseases.

PRIOR ART DOCUMENTS

Patent Documents

Non-Patent Document 1: F. S. Kaplan et al., Methods Enzymol 484, 357 (2010)
Non-Patent Document 2: E. M. Shore, F. S. Kaplan, Bone 43, 427 (2008)
Non-Patent Document 3: T. Fukuda et al., J Biol Chem 284, 7149 (2009)
Non-Patent Document 4: P. C. Billings et al., J bone Miner Res 23, 305 (2008)
Non-Patent Document 5: J. L. Fiori, P. C. Billings, L. S. de la Pena, F. S. Kaplan, E. M. Shore, J Bone Miner Res 21, 902 (2006)
Non-Patent Document 6: F. S. Kaplan et al., Hum Mutat 30, 379 (2009)
Non-Patent Document 7: A. B. Shafritz et al., N Engl J Med 335, 555 (1996)
Non-Patent Document 8: Q. Shen et al., J Clin Invest 119, 3462 (2009)
Non-Patent Document 9: E. M. Shore et al., Nat Genet 38, 525 (2006)
Non-Patent Document 10: H. Furuya et al., Am J Med Genet A 146A, 459 (2008)
Non-Patent Document 11: T. Fukuda et al., Biochem Biophys Res Commun 377, 905 (2008).
Non-Patent Document 12: Yu P B et al., Nat Med. 2008 December; 14 (12): 1363-9

SUMMARY OF INVENTION

Object to be Solved by the Invention

Under the current circumstances, drug selection and drug efficacy testing are being carried out in drug screening systems using general culture cell lines, genetically abnormal transgenic mice, and the like in the development of drugs for intractable diseases such as fibrodysplasia ossificans progressiva. However, the use of such techniques makes experimental procedures troublesome, resulting in obviously time-consuming drug efficacy evaluation, which is problematic. Further, medicinal effects are not evaluated using cells derived from a patient of interest in such a conventional drug screening system. This raises a problem that there is a persistent concern whether or not selected drugs can actually function as effective drugs.

The object of the present invention is to provide a method for screening a substance capable of promoting induction of induced pluripotent stem cells from cells derived from an individual affected by a disease for which it is impossible to produce induced pluripotent stem cells simply by introducing reprogramming genes.

Means for Solving the Object

As a result of intensive studies in order to achieve the above object, the present inventors found that substantially no induced pluripotent stem cells can be established even by introducing four factors (Oct4, Sox2, KLF4, and cMyc) as reprogramming genes into fibroblasts derived from patients and especially fibrodysplasia ossificans progressiva patients to cause induction of induced pluripotent stem cells, and at the same time, they found that induced pluripotent stem cells can be efficiently established through induction of induced pluripotent stem cells in the presence of LDN193189 known as an ALK2 inhibitor. It is known that LDN-193189 which is an inhibitor specific to BMP type I receptor kinase alleviates ectopic osteogenesis and functional disorder which are major symptoms of fibrodysplasia ossificans progressiva (Non-Patent Document 12). Further, the present inventors found that substantially no induced pluripotent stem cells can be established even by introducing four factors (Oct4, Sox2, KLF4, and cMyc) as reprogramming genes into fibroblasts derived from patients and especially patients affected by Krabbe disease which is a lysosomal disease to cause induction of induced pluripotent stem cells, and at the same time, they found that the induced pluripotent stem cells can be efficiently established through induction of induced pluripotent stem cells in the presence of sodium butyrate.

The present invention has been completed based on the above findings.

(1) A method for screening a substance, which comprises culturing cells derived from an individual affected by a disease for which it is impossible to produce induced pluripotent stem cells simply by introducing reprogramming genes, the cells being transfected with reprogramming genes, in the presence of test substances, and selecting a test substance capable of promoting induction of induced pluripotent stem cells from the cells.
(2) The method according to (1), wherein the disease is caused by a change in kinase activity.
(3) The method according to (1) or (2), wherein the disease is caused by a change in activity of activin receptor-like kinase 2.
(4) The method according to any one of (1)-(3), wherein the disease is fibrodysplasia ossificans progressiva, mitochondrial disease, or lysosomal disease.
(5) The method according to any one of (1)-(4), wherein the disease is fibrodysplasia ossificans progressive or lysosomal disease.
(6) The method according to any one of (1)-(5), wherein the disease is fibrodysplasia ossificans progressiva or Krabbe disease.
(7) The method according to any one of (1)-(6), wherein the cells are human cells.
(8) The method according to (7), wherein the cells contain a gene encoding an amino acid sequence derived from the amino acid sequence shown in SEQ ID NO: 2 by substitution of arginine at position 206 with histidine.
(9) The method according to (7) or (8), wherein the cells contain a gene encoding an amino acid sequence derived from the amino acid sequence shown in SEQ ID NO: 2 by substitution of glycine at position 356 with aspartic acid.
(10) The method according to any one of (1)-(9), wherein the reprogramming genes are the Oct3/4 gene, Klf4 gene, Sox2 gene, and c-Myc gene.
(11) The method according to any one of (1)-(10), wherein the cells are fibroblasts.
(12) The method according to any one of (1)-(11), which further comprises selecting a test substance capable of inhibiting activin receptor-like kinase 2.
(13) The method according to any one of (1)-(12), which is a method for screening a therapeutic agent of the disease.
(14) The method according to any one of (1)-(13), which is a method for screening a therapeutic agent of fibrodysplasia ossificans progressiva, mitochondrial disease, or lysosomal disease.
(15) The method according to any one of (1)-(14), which is a method for screening a therapeutic agent of fibrodysplasia ossificans progressiva or lysosomal disease.
(16) The method according to any one of (1)-(15), which is a method for screening a therapeutic agent of fibrodysplasia ossificans progressiva or Krabbe disease.
(17) A method for producing induced pluripotent stem cells, which comprises culturing cells derived from an individual affected by a disease for which it is impossible to produce induced pluripotent stem cells simply by introducing reprogramming genes, the cells being transfected with reprogramming genes, in the presence of a substance capable of promoting induction of induced pluripotent stem cells from the cells.
(18) The method according to (17), wherein the disease is caused by a change in kinase activity.
(19) The method according to (17) or (18), wherein the disease is caused by a change in activity of activin receptor-like kinase 2.
(20) The method according to any one of (17)-(19), wherein the disease is fibrodysplasia ossificans progressiva, mitochondrial disease, or lysosomal disease.
(21) The method according to any one of (17)-(20), wherein the disease is fibrodysplasia ossificans progressive or lysosomal disease.
(22) The method according to any one of (17)-(21), wherein the disease is fibrodysplasia ossificans progressiva or Krabbe disease.
(23) The method according to any one of (17)-(22), wherein the cells are human cells.
(24) The method according to (23), wherein the cells contain a gene encoding an amino acid sequence derived from the amino acid sequence shown in SEQ ID NO: 2 by substitution of arginine at position 206 with histidine.
(25) The method according to (23) or (24), wherein the cells contain a gene encoding an amino acid sequence derived from the amino acid sequence shown in SEQ ID NO: 2 by substitution of glycine at position 356 with aspartic acid.
(26) The method according to any one of (17)-(25), wherein the reprogramming genes are the Oct3/4 gene, Klf4 gene, Sox2 gene, and c-Myc gene.
(27) The method according to any one of (17)-(26), wherein the cells are fibroblasts.

Advantageous Effects of Invention

According to the present invention, a substance capable of promoting induction of induced pluripotent stem cells can be efficiently screened even for a disease for which it is impossible to produce induced pluripotent stem cells simply by introducing reprogramming genes by a conventional method. Further, according to the present invention, it becomes possible to provide a method for screening a substance that can be used for a drug screening system whereby highly reliable drug candidates can be conveniently and efficiently obtained even in the case of a disease for which it is impossible to produce induced pluripotent stem cells simply by introducing reprogramming genes.

BRIEF DESCRIPTION OF DRAWINGS

FIG. 1 show the results of examining formation of iPS cells derived from FOP patients. FIG. 1A shows efficiency (%) of formation of iPS cells from FOP patients and healthy volunteers; iPS colonies were confirmed based on AP-positive and ES-like morphology (typical morphology). FIG. 1B shows the results of AP staining of iPS cell colonies in a 60-mm petri dish. FIG. 1C shows morphology of iPS cell colonies (scale unit: 200 μm). FIG. 1D shows the numbers of typical and atypical iPS cell colonies in FOP and controls and the ratio thereof.

FIG. 2A shows the effects of improving iPS cell colony formation by treatment with LDN-193189 (LDN) and dorsomorphin which are ALK2 inhibitors; iPS colonies were confirmed based on AP-positive and ES-like morphology. Left and right panels correspond to patients F2 and patients F4. FIG. 2B shows phase contrast images of FOP-derived iPS cells generated from individual patients treated with LDN (scale unit: 200 FIG. 2C shows the results of RT-PCR analysis of Sendai virus and human ES markers. iPS F1-1, iPS F2-1, and iPS F4-1 correspond to iPS cell lines derived from patients F1, F2, and F4, respectively (201B7: a control human iPS cell line; SeV (+): SeV-infected fibroblasts). FIG. 2D shows the results of immunofluorescent staining and AP staining with the use of pluripotency markers for FOP-derived iPS cell lines (scale unit: 200 μm). FIG. 2E shows the results of examining spontaneous differentiation of FOP-derived iPS cell lines in the absence of LDN. "Undifferentiated (U)" represents typical iPS colonies, "Partially differentiated (P)" represents partially differentiated colonies, and "Differentiated (D)" represents completely differentiated colonies (upper panel images). FIG. 2E, also shows the numbers of three types of colonies and the ratio thereof for FOP-derived iPS cell lines cultured in the presence or absence of inhibitors (middle and lower panels) (scale unit: 200 μm). FIG. 2F shows the results of immunofluorescent staining with the use of differentiation markers for FOP-derived iPS cell lines cultured in the absence of LDN. FIG. 2F also shows typical data obtained from iPS cell lines F2-F6 by staining four types of iPS cell lines (scale unit: 200 μm). FIG. 2G shows the results of quantitative RT-PCR regarding expression of genes associated with pluripotency and differentiation. Data are standardized with respect to GAPDH and expressed as relative expression levels to those in 201B7 human iPS cell lines cultured in the absence of LDN.

FIG. 3A shows an experimental plan of treatment with LDN. LDN treatment is carried out during the period shown in the figure for iPS cell induction culture. FIG. 3B shows the results of AP staining of iPS cell colonies derived from the patients F2 (left) and the healthy volunteer N1 (right) subjected to LDN treatment in a 60-mm petri dish during the periods shown in FIG. 3 (A) at three LDN concentrations (0 nM, 30 nM, and 200 nM). "d1-d7," "d1-d30," and "d8-d30" correspond to LDN treatment periods of day 1 to day 7, day 1 to day 30, and day 8 to day 30, respectively. FIG. 3C shows efficiency of formation of iPS cell colonies treated with LDN for each period. Typical AP-positive colonies were counted on day 30. The horizontal axis of the graph represents LDN treatment periods 1 to 7; the numerals 1, 2, 3, 4, 5, 6, and 7 represent "d1-d30," "d1-d7," "d1-d30," "d8-d30," "d8-d14," "d15-d21," and "d22-d30" respectively (see FIG. 3A).

FIG. 4 show the results of examining ALK2 inhibitors. FIG. 4A shows the results of examining general gene expression patterns of normal iPS cells and FOP-derived iPS cells. A scatter diagram shows general gene expression patterns of the iPS cell lines N3-1, F1-1, F2-1, and F4-1 in the presence or absence of LDN-193189. FIG. 4B shows the structures of LDN-193189 and dorsomorphin.

FIG. 5A shows the results of genomic nucleotide sequencing of the ALK2 gene in FOP-derived iPS cell lines ("GTGGCTCNCCAGATT" disclosed as SEQ ID NO: 57, "TTTCAGGCCTGGC" disclosed as SEQ ID NO: 58, "GTGGCTCGCCAGATT" disclosed as SEQ ID NO: 59, and "TTTCAGNCCTGGC" disclosed as SEQ ID NO: 60). Each arrow shows a 617G>A (R206H) or 1067G>A (G356D) mutation. FIG. 5B shows phase contrast images of FOP-derived iPS cells treated with dorsomorphin (DM): left panel: patient-F2-derived iPS cells; right panel: patient-F4-derived iPS cells (scale unit: 200 μm). FIG. 5C shows the numbers of three types of colonies and the ratio thereof for FOP-derived iPS cell lines. The iPS F2-1 and iPS F4-2 cells were cultured in the presence or absence of DM. The "Undifferentiated (U)," "Partially differentiated (P)," and "Differentiated (D)" colonies are defined as described in FIG. 2E (scale unit: 200 μm). FIG. 5D shows the results of immunoblot analysis of phosphorylated Smad1/5/8 for normal control iPS cells (201B7) and FOP-derived iPS cells (F2-1 and F4-1) treated in the absence or presence of LDN-193189 (LDN). The relative levels of Smad1/5/8 phosphorylation in iPS F2-1, F4-1, and 201B7 treated with BMP-4 are higher than those obtained for 201B7 cells alone, indicating that such Smad1/5/8 phosphorylation is inhibited by treatment with LDN. 201B7 iPS cells treated in the presence or absence of 10-ng/mL BMP-4 were used as a negative control and a positive control for Smad1/5/8 phosphorylation, respectively. FIG. 5E shows the results of examining the effects of DM upon Smad1/5/8 phosphorylation in FOP-derived iPS cells. Smad1/5/8 phosphorylation in FOP-derived iPS cells (F2-1 and F4-2) is inhibited by treatment with DM as in the case of LDN. The relative levels of phosphorylated Smad1/5/8 are standardized with respect to total Smad1.

FIG. 6A shows Venn diagrams of the expression genes upregulated or downregulated at at least two-fold different levels which are observed in common for iPS F2-1 and F2-2 cultured in the absence of LDN. Of 54,675 genes, 1,417 expression genes are upregulated and 394 genes are downregulated in common for F2 iPS cell lines. FIG. 6B shows Venn diagrams of the expression genes upregulated or downregulated at at least two-fold different levels which are observed in common for iPS F1-1, F2 (F2-1 and F2-2), and F4-1 cultured in the absence of LDN. When the gene expression profiles of these iPS cell lines are compared with each other, it is shown that the expression is upregulated in common in 516 genes, and the expression is downregulated in common in 85 genes.

EMBODIMENTS FOR CARRYING OUT THE INVENTION

Figure 2:
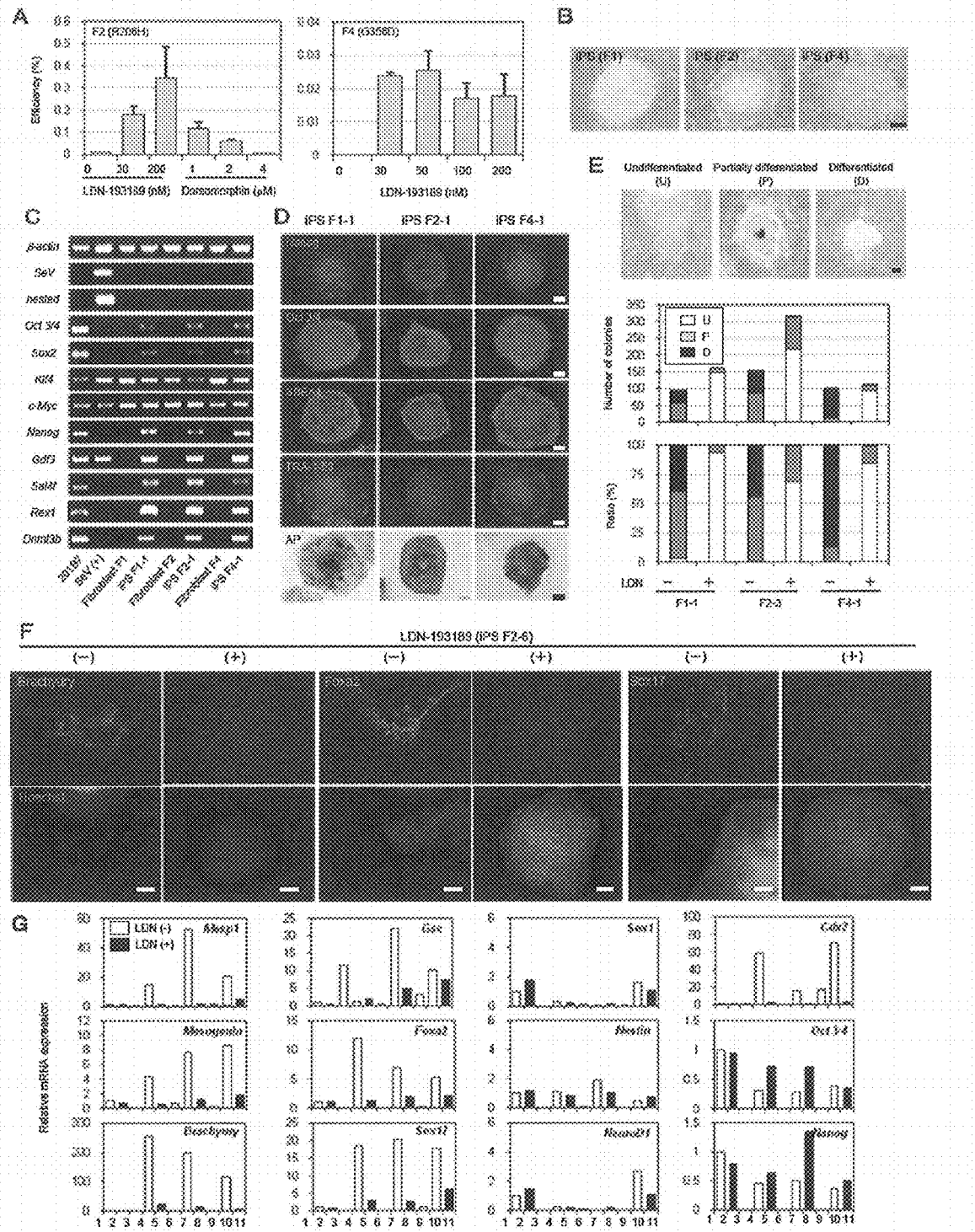
FIG. 2 show the results of examining generation and maintenance of iPS cells induced from FOP fibroblasts by ALK2 inhibitor treatment.

The present invention relates to a method for screening a substance, which comprises culturing cells derived from an individual affected by a disease for which it is impossible to produce induced pluripotent stem cells simply by introducing reprogramming genes, the cells being transfected with the reprogramming genes, in the presence of test substances; and selecting a test substance capable of promoting induction of the cells into induced pluripotent stem cells.

According to the present invention, the term "disease for which it is impossible to produce induced pluripotent stem cells simply by introducing reprogramming genes" refers to a disease for which it is impossible to produce induced pluripotent stem cells (iPS cells) or which allows generation of iPS cells only with low efficiency even by introducing reprogramming genes described below into cells (somatic cells) derived from a patient affected by the disease to cause induction of iPS cells by a conventional method. More specifically, the term refers to a disease which does not allow formation of iPS cell colonies on medium even by introducing reprogramming genes into cells derived from the disease and culturing the cells in different types of iPS medium to cause induction of induced pluripotent stem cells or a disease which allows formation of iPS cell colonies on medium with lower frequently compared with a case in which iPS cells are induced from cells derived from a healthy individual. Furthermore specifically, the term refers to a disease which causes a decrease in the number of colonies formed by introducing reprogramming genes (and especially the Oct3/4 gene, Klf4 gene, Sox2 gene, and c-Myc gene) into cells affected by the disease and seeding the cells on medium (1-2×10$^5$ cells per 100-mm petri dish) to cause induction of iPS cells, compared with a case in which iPS cells are induced from cells derived from a healthy individual. For example, the term "disease for which it is impossible to produce induced pluripotent stem cells simply by introducing reprogramming genes" refers to a disease which causes a decrease in efficiency of iPS cell colony formation compared with that in the case of a healthy individual-derived control, and for which the number of formed iPS cell colonies is 50 or less, preferably 10 or less, more preferably 10 or less, particularly preferably 5 or less, 4 or less, 3 or less, 2 or less, 1 or less, or 0.

Within the scope of the above definition, examples of the disease according to the present invention include, but are not particularly limited to, a disease for which it is impossible to induce iPS cells from cells derived from an individual affected by the disease due to abnormalities in the disease gene (e.g., deletion of the disease gene or mutation such as amino acid deletion, substitution, and/or addition in an amino acid sequence encoded by the disease gene) or abnormal expression of the gene (e.g., loss of expression, reduced expression, or overexpression).

More specifically, examples of the disease according to the present invention include a disease that shows abnormal kinase activity (and especially increased activity) compared with that in normal individuals and is developed in response to the abnormal activity. Examples of kinase include activin receptor-like kinase 2 (ALK2). Example of such abnormal kinase activity include: an example in which kinase activity decreases or increases compared with that in normal individuals; and an example in which kinase is not normally regulated by regulatory factors and thus kinase is always activated or inactivated in disease-affected individuals while kinase activity is controlled by specific regulatory factors in a given mode (of "on" or "off" activity) in normal individuals.

Specific examples of the disease according to the present invention include fibrodysplasia ossificans progressiva (FOP), mitochondrial diseases [e.g., chronic progressive external ophthalmoplegia (CPEO), myoclonus epilepsy associated with ragged-red fibers (MERRF) (also referred to as "Fukuhara disease"), and mitochondrial encephalomyopathy, lactic acidosis, stroke-like episodes (MELAS)], hematopoietic organ tumor (e.g., leukemia), and lysosomal diseases. Specific examples of lysosomal diseases include Krabbe disease. Krabbe disease is classified into the early infantile type (age of onset: 3-6 months old), late infantile type (age of onset: 6 months to 3 years old), juvenile type (age of onset: 3-10 years old), and adult type (age of onset: 10-35 years old). The disease according to the present invention is preferably fibrodysplasia ossificans progressiva (FOP), mitochondrial disease, or lysosomal disease, more preferably fibrodysplasia ossificans progressiva (FOP) or lysosomal disease, and particularly preferably fibrodysplasia ossificans progressiva (FOP) or Krabbe disease. Krabbe disease is preferably infantile Krabbe disease.

The ALK2 gene (ACVR1) is known as the disease gene of FOP. The nucleotide sequence of mRNA of the human ALK2 gene (Homo sapiens activin A receptor, type I (ACVR1), transcript variant 1, mRNA) has been publicly available as NCBI Accession No.: NM_001105. The nucleotide sequence of the CDS region is shown in SEQ ID NO: 1, and the amino acid sequence thereof is shown in SEQ ID NO: 2.

When healthy volunteers and FOP patients are compared in terms of the ALK2 gene, the nucleotide at position 617 of the nucleotide sequence of the CDS region is guanine (G) in healthy volunteers, while adenine (A) replaces guanine (G) in FOP patients. This nucleotide mutation causes arginine at position 260 to be replaced by histidine (R206H) in the amino acid sequence of a protein encoded by the ALK2 gene. Further, it has been known that there is a rare case of mutation of the ALK2 gene in FOP patients in which adenine (A) replaces guanine (G) at position 1067 in the nucleotide sequence of the CDS region, and asparagine replaces glycine at position 356 (G356D) in the amino acid sequence of the CDS region. ALK2 functions as a single transmembrane receptor of BMP (bone morphogenetic protein) known as a growth causing bone tissue induction. When the extracellular domain of ALK2 binds to BMP, ALK2 is activated to transduce intracellular osteogenesis signaling. It has been revealed that ALK2 which is not bound to BMP is inactivated (in the "off" state) in healthy volunteers, while on the other hand, ALK2 is activated (in the "on" state) even when it is not bound to BMP in FOP patients. It is considered that ALK2 is always activated in FOP, which results in signal transduction for promoting osteogenesis and causes progress in ectopic osteogenesis.

According to the present invention, the "individual" is not particularly limited; however, it is preferably a mammal and more preferably a human.

According to the present invention, the type of "cells" is not particularly limited; however, cells are specifically somatic cells. Cells collected from any tissue or culture cells obtained by culturing such collected cells can be used. According to the present invention, somatic cells include all cells, excluding germ cells, which constitute the living body. The somatic cells may be differentiated somatic cells or undifferentiated stem cells. In addition, the term "derived" used in the present invention means that cells sampled from an individual may be directly used for the screening method of the present invention, or a cultured cell line established by culturing the sampled cells may be used for the screening method of the present invention. Specific examples of the cells used in the present invention include fibroblasts obtained by culturing skin sampled from a disease-affected individual. Further, as the cells used in the present invention, cells comprising the gene encoding ALK2 having the above mutation (R206H and/or G356D) can be used. Specifically, human cells comprising the gene encoding ALK2 having the R206H and/or G356D mutation in the amino acid sequence shown in SEQ ID NO: 2, can be used.

According to the screening method of the present invention, cells obtained by introducing reprogramming genes into cells derived from the above disease-affected individual are cultured in medium used for induction and maintenance of induced pluripotent stem cells in the presence of a test substance, and a test substance capable of promoting induction of induced pluripotent stem cells from the cells is selected.

According to the method of the present invention, at least one type of reprogramming genes is introduced into cells. Reprogramming genes encode reprogramming factors that function to reprogram somatic cells to obtain iPS cells. Examples of a combination of reprogramming genes include, but are not limited to, the following combinations.

(i) Oct gene, Klf gene, Sox gene, and Myc gene
(ii) Oct gene, Sox gene, NANOG gene, and LIN28 gene
(iii) Oct gene, Klf gene, Sox gene, Myc gene, hTERT gene, and SV40 large T gene
(iv) Oct gene, Klf gene, and Sox gene Each of the Oct gene, Klf gene, Sox gene, and Myc gene includes a plurality of family genes. Specific examples of family genes that can be used are disclosed in WO2007/069666 (see pp. 11-13). Specific examples thereof are described below.

Specific examples of genes included in the Oct gene are Oct3/4 (NM_002701), Oct1A (NM_002697), and Oct6 (NM_002699) (the NCBI accession of a human gene is shown in the parentheses). Of these, Oct3/4 is preferable. Oct3/4 is a transcription factor belonging to the POU family and known as an undifferentiation marker. It has been also reported that Oct3/4 is involved in pluripotency maintenance.

Specific examples of genes included in the Klf gene are Klf1 (NM_006563), Klf2 (NM_016270), Klf4 (NM_004235), and Klf5 (NM_001730) (the NCBI accession of a human gene is shown in the parentheses). Of these, Klf4 is preferable. It has been reported that Klf4 (0 like factor-4) is a tumor-suppression factor.

Specific examples of genes included in the Sox gene are Sox1 (NM_005986), Sox2 (NM_003106), Sox3 (NM_005634), Sox7 (NM_031439), Sox15 (NM_006942), Sox17 (NM_0022454), and Sox18 (NM_018419) (the NCBI accession of a human gene is shown in the parentheses). Of these, Sox2 is preferable. Sox2 is a gene that is expressed in the early development process and encodes a transcription factor.

Specific examples of genes included in the Myc gene are c-Myc (NM_002467), N-Myc (NM_005378), and L-Myc (NM_005376) (the NCBI accession of a human gene is shown in the parentheses). Of these, c-Myc is preferable. It has been reported that c-Myc is a transcription control factor involved in cell differentiation and growth and thus it is associated with pluripotency maintenance.

The above genes are present in common in mammals including humans. According to the present invention, a gene of any mammal (e.g., a mammal such as a human, mouse, rat, or monkey) can be used. In addition, it is also possible to use a mutant gene derived from the wild-type gene by mutation such as substitution, insertion, and/or deletion of one or more nucleotides (e.g., 1-30, preferably 1-20, more preferably 1-10, and further preferably 1-5, and particularly preferably 1-3 nucleotides) and having functions comparable to those of the wild-type gene.

According to the present invention, it is particularly preferable to use, as reprogramming genes, a combination of the Oct3/4 gene, Klf4 gene, Sox2 gene, and c-Myc gene.

A method for introducing reprogramming genes into cells is not particularly limited as long as the introduced reprogramming genes are allowed to be expressed to achieve reprogramming of the cells. For example, the reprogramming genes can be introduced into the cells using an expression vector containing at least one reprogramming gene. When at least two types of reprogramming genes are introduced into cells using a vector, it is possible to incorporate at least two types of reprogramming genes into a single expression vector and introduce the expression vector into cells. Alternatively, it is also possible to prepare at least two types of expression vectors, into each of which a different reprogramming gene has been incorporated, and introduce the vectors into cells.

The types of expression vectors are not particularly limited. Thus, either viral vectors or plasmid vectors may be used; however, viral vectors are preferable. Examples of viral vectors that can be used in the present invention include retrovirus vectors (including lentivirus vectors), adenovirus vectors, adeno-associated viral vectors, and Sendai virus vectors. Of these, Sendai virus vectors are preferable.

According to the method of the present invention, cells transfected with reprogramming genes are cultured in the presence of test substances. In this step, the cells can be cultured by adding test substances to any medium that can be used for induction or maintenance of induced pluripotent stem cells. Specifically, media that can maintain undifferentiation potency and pluripotency of ES cells or induced pluripotent stem cells are known in the art and thus a combination of appropriate media can be used. Specific examples of medium that can be used for culturing cells transfected with reprogramming genes in the presence of test substances according to the method of the present invention include ES medium, MEF-conditioned ES medium which is a supernatant obtained by culturing mouse embryonic fibroblasts for 24 hours in ES medium supplemented with 10 ng/ml FGF-2 (hereinafter referred to as "MEF-conditioned ES medium"), and DMEM medium supplemented with given amounts of KnockOut Serum Replacement (KSR) (Invitrogen) and/or bFGF. According to the present invention, a variety of growth factors, cytokines, hormones, and the like (e.g., components involved in growth maintenance of human ES cells such as FGF-2, TGFb-1, activin A, noggin (Nanoggin), BDNF, NGF, NT-1, NT-2, and NT-3) may be added to medium used for culturing cells transfected with reprogramming genes.

When cells transfected with reprogramming genes are cultured in the presence of test substances, appropriate feeder cells may be used according to the present invention. In general, feeder cells used in the present invention are not particularly limited as long as the cells can induce or maintain pluripotent stem cells. Specific examples of feeder cells include MEF cells. In addition, feeder cells may be allowed to lose cell growth ability through mitomycin C treatment or exposure to radiation before use. MEF cells (obtained from ICR mice) are registered with the ATCC as catalog number: ATCC#SCRC-1046. In addition, MEF cells can be obtained in accordance with the reference (Nagy A, et al. Manipulating the Mouse Embryo: A Laboratory Manual. Third Edition Cold Spring Harbor Press; 2003).

Any substances can be used as the test substances used in the present invention. The types of test substances are not particularly limited. Test substances may be low-molecular-weight compounds, compounds present in natural extract, or synthetic peptides. Alternatively, test compounds may be in the form of compound libraries, phage display libraries, or combinatorial libraries. Test substances are preferably low-molecular-weight compounds or in the form of compound libraries of low-molecular-weight compounds. Construction of compound libraries is known in the art. It is also possible to use commercially available compound libraries.

As described above, cells transfected with reprogramming genes are cultured in the presence of test substances such that a test substance capable of promoting induction of induced pluripotent stem cells from the cells can be selected. It is possible to determine whether or not induction of induced pluripotent stem cells is promoted in the following manner. For example, a negative control group prepared by culturing the cells of the present invention in medium free from a test substance and a test sample group prepared by culturing the cells transfected with reprogramming genes of the present invention in medium supplemented with a test substance are compared with each other. If induced pluripotent stem cells are observed on the medium of the test sample group more frequently than those observed in the negative control group, the test substance can be selected as a substance capable of promoting induction of induced pluripotent stem cells.

It is possible to confirm whether or not induction of induced pluripotent stem cells has occurred by, for example, visually observing formation of iPS cell colonies on medium. More specifically, a negative control group prepared by culturing the cells transfected with reprogramming genes of the present invention in medium free from a test substance and a test sample group prepared by culturing the cells transfected with reprogramming genes of the present invention in medium supplemented with a test substance are compared with each other. If typical colonies of induced pluripotent stem cells are observed on the medium of the test sample group more frequently than those observed in the negative control group, the test substance can be selected as a substance capable of promoting induction of induced pluripotent stem cells. In general, edges of iPS cell colonies are clearly observed, indicating high cell densities. A person skilled in the art can visually confirm iPS cell colonies. In addition, colonies showing atypical morphology that is different from morphology of iPS cell colonies is sometimes observed in the negative control group prepared by culturing the cells transfected with reprogramming genes of the present invention in medium free from a test substance, or in a case in which a test substance does not promote induction of induced pluripotent stem cells. Therefore, microscopic observation can be carried out according to need.

Further, it is also possible to determine whether or not induction of induced pluripotent stem cells has occurred by detecting, as an indicator for iPS cell induction, alkaline phosphatase activity of formed cells (colonies). In a case in which cells (colonies) detected as having alkaline phosphatase activity are observed in the test sample group more frequently than those in negative control group, the test substance can be selected as a substance capable of promoting induction of induced pluripotent stem cells.

Furthermore, it is also possible to determine whether or not induction of induced pluripotent stem cells has occurred by detecting, as an indicator for iPS cell induction, expression of pluripotency markers in formed cells (colonies). If the expression levels of pluripotency markers in the test sample group are confirmed to be higher than those in the negative control group, the test substance can be selected as a substance capable of promoting induction of induced pluripotent stem cells. Examples of pluripotency markers include Oct3/4, Sox2, Klf4, C-Myc, Nanog, Gdf3, Sall4f, Rex1, Dnmt3b, SSEA4, and TRA-1-60. Meanwhile, it is also possible to determine whether or not formed cells (colonies) are induced pluripotent stem cells by detecting cell differentiation markers. For example, it may be determined that cells (colonies) detected as expressing cell differentiation markers are not induced pluripotent stem cells. Examples of cell differentiation markers include: mesodermal markers such as Brachyury (Brachyury), Mesogenin, and Mesp1; endodermal markers such as Sox17 and Foxa2; trophectodermal markers such as Cdx2; neuroectodermal markers such as Nestin; and nerve cell markers such as Sox1 and NeuroD1.

As described above, according to the screening method of the present invention, even in the case of a disease for which it is impossible to produce induced pluripotent stem cells simply by introducing reprogramming genes by a conventional method, it is possible to screen a substance that can efficiently induce iPS cells from cells derived from an individual affected by the disease. A substance obtained through screening can normalize or improve the feature particular to the disease that induction of induced pluripotent stem cells is impossible or difficult. Therefore, the substance is likely to be available as a therapeutic agent of the disease of interest. That is, as described above, the method of the present invention can be used for a drug screening system in the development of therapeutic agents of a disease for which it is impossible to produce induced pluripotent stem cells simply by introducing reprogramming genes.

In one embodiment of the present invention, when using cells, which are derived from an individual affected by the aforementioned disease that shows abnormal kinase activity (and especially increased activity) compared with that in normal individuals and is developed in response to the abnormal activity, in the method of the present invention, it is possible to select a substance capable of inhibiting activity of kinase (e.g., activin receptor-like kinase 2) from among test substances selected as the substance capable of promoting induction of induced pluripotent stem cells from the cells.

Further, in another embodiment of the present invention, a "method for producing induced pluripotent stem cells, which comprises culturing cells derived from an individual affected by a disease for which it is impossible to produce induced pluripotent stem cells simply by introducing reprogramming genes, the cells being transfected with reprogramming genes, in the presence of a substance capable of promoting induction of induced pluripotent stem cells from the cells" is provided.

According to the method for producing induced pluripotent stem cells of the present invention, the terms "disease for which it is impossible to produce induced pluripotent stem cells simply by introducing reprogramming genes," "individual," "derived," "cells," and "reprogramming gene" are defined as described above for the method for screening a substance according to the present invention. The method for producing induced pluripotent stem cells can be carried out in accordance with the method for screening a substance. An example of the "disease for which it is impossible to produce induced pluripotent stem cells simply by introducing reprogramming genes" is preferably fibrodysplasia ossificans progressiva, mitochondrial disease, or lysosomal disease and particularly preferably fibrodysplasia ossificans progressiva or Krabbe disease. Krabbe disease is preferably infantile Krabbe disease.

In the method for producing induced pluripotent stem cells of the present invention, a substance selected by the method for screening a substance of the present invention can be used as a "substance capable of promoting induction of cells into induced pluripotent stem cells". For example, if a disease of interest is caused by increased kinase activity, a kinase inhibitor can be used. If a disease of interest is fibrodysplasia ossificans progressiva, an activin receptor-like kinase 2 inhibitor can be used. For example, LDN-193189 and/or dorsomorphin described in the Examples below can be used. In addition, if a disease of interest is lysosomal disease (e.g., Krabbe disease), for example, butyric acid and/or butyrate (preferably sodium butyrate) can be used as the "substance capable of promoting induction of cells into induced pluripotent stem cells."

The present invention is described below in more detail in the following Examples. However, the present invention is not specifically limited to the Examples.

EXAMPLES

Example 1

(A) Materials and Method (1) Production of Skin-Derived Fibroblasts

Fibroblasts were produced from skin biopsy explants of FOP patients and healthy volunteers with informed consent from them in accordance with the protocol approved by the ethical committee. Skin samples obtained from the patients and healthy volunteers were finely minced and cultured in D-MEM medium supplemented with 10% fetal bovine serum (FBS). After fibroblasts were observed to have grown, the fibroblasts were allowed to proliferate for induction into iPS cells.

(2) Maintenance and Generation of iPS Cells

Human iPS cells were maintained on MEF feeder cells treated with mitomycin C (MMC) in human iPS medium containing DMEM/F12 (Sigma) supplemented with 20% KNOCKOUT (trademark) serum replacement (KSR, Invitrogen), 2 mM L-glutamine, $1\times10^{-4}$ M non-essential amino acid (NEAA, Sigma), $1\times10^{-4}$ M 2-mercaptoethanol (Sigma), 0.5% penicillin and streptomycin (Nacalai Tesque, Japan), and a 5 ng/mL basic fibroblast growth factor (bFGF, Wako, Japan). ALK2 inhibitors such as LDN-193189 (STEMGENT) and dorsomorphin (Sigma) were added to the human iPS medium in some experiments in this Example.

According to the method described in N. Fusaki, H. Ban, A. Nishiyama, K. Saeki, M. Hasegawa, Proc. Jpn. Acad. Ser., B. Phys. Biol. Eci., 85, 348 (2009), iPS cells were generated from human-derived fibroblasts. The human fibroblasts were seeded on a 6-well plate ($5\times10^5$ cells/well) on the day before infection. The cells were infected with Sendai virus (SeV) vectors described below at a multiplicity of infection (MOI) of 3. Trypsin was used to recover the infected fibroblasts on day 7 after infection. The cells were seeded on MMC-treated MEF feeder cells ($5.4\times10^4$ cells per 60-mm petri dish or 1 or $2\times10^5$ cells per 100-mm petri dish). On the next day, the medium was replaced by human iPS cell medium. On day 30 after infection, colonies were isolated and re-cultured in human iPS cell medium.

(3) Construction and Detection of Sendai Virus (SeV) Vectors

SeV vectors containing the Oct3/4 gene, Sox2 gene, Klf4 gene, and c-Myc gene were constructed in the manner described in N. Fusaki, H. Ban, A. Nishiyama, K. Saeki, M. Hasegawa, Proc. Jpn. Acad. Set, B. Phys. Biol. Eci., 85, 348 (2009). Nested PCR was performed to detect the SeV genome. Total RNA (1 microgram) extracted from skin fibroblasts and iPS cells was reverse transcribed into cDNA. Next, a pair of SeV specific primers were used to amplify cDNA. A 1/10 volume of the PCR products were further amplified using a pair of nested PCR primers. Table 1 lists primer sequences and amplification conditions.

TABLE 1

| Gene | Sequence (F: forward primer; R: reverse primer) | Annealing temperature (° C.) | Number of cycles | Amplification product size (bp) |
|---|---|---|---|---|
| SeV | F: GGATCACTAGGTGATATCGAGC (SEQ ID NO: 3) R: ACCAGACAAGAGTTTAAGAGATATGTATC (SEQ ID NO: 4) | 58 | 30 | 181 |
| Nested | F: TCGAGCCATATGACAGCTCG (SEQ ID NO: 5) R: GAGATATGTATCCTTTTAAATTTTCTTGTCTTCTTG (SEQ ID NO: 6) | 58 | 30 | 148 |
| Oct 3/4 | F: GACAGGGGGAGGGGAGGAGCTAGG (SEQ ID NO: 7) R: CTTCCCTCCAACCAGTTGCCOCAAAC (SEQ ID NO: 8) | 55 | 33 | 144 |
| Sox2 | F: GGGAAATGGGAGGGGTGCAAAAGAGG (SEQ ID NO: 9) R: TTGCGTGAGTGTGGATGGGATTGGTG (SEQ ID NO: 10) | 55 | 33 | 151 |

TABLE 1-continued

| Gene | Sequence (F: forward primer; R: reverse primer) | Annealing temperature (° C.) | Number of cycles | Amplification product size (bp) |
|---|---|---|---|---|
| Klf4 | F: GATTACGCGGGCTGCGGCAAAACCTACACA (SEQ ID NO: 11)<br>R: TGATTGTAGTGCTTTCTGGCTGGGCTCC (SEQ ID NO: 12) | 56 | 35 | 357 |
| c-Myc | F: GCGTCCTGGGAAGGGAGATCCGGAGC (SEQ ID NO: 13)<br>R: TTGAGGGGCATCGTCGCGGGAGGCTG (SEQ ID NO: 14) | 56 | 33 | 328 |
| Nanog | F: CAGCCCCGATTCTTCCACCAGTCCC (SEQ ID NO: 15)<br>R: CGGAAGATTCCCAGTCGGCTTCACC (SEQ ID NO: 16) | 60 | 30 | 391 |
| Gdf3 | F: CTTATGCTACGTAAAGGAGCTGGG (SEQ ID NO: 17)<br>R: GTGCCAACCCAGGTCCCGGAAGTT (SEQ ID NO: 18) | 56 | 35 | 631 |
| Rex1 | F: CAGATCCTAAACAGCTCGCAGAAT (SEQ ID NO: 19)<br>R: GCGTACGCAAATTAAAGTCCAGA (SEQ ID NO: 20) | 55 | 30 | 306 |
| Sall4f | F: AAACCCCAGCACATCAACTC (SEQ ID NO: 21)<br>R: GTCATTCCCTGGGTGGITC (SEQ ID NO: 22) | 58 | 30 | 138 |
| Dnmt3b | F: TGCTGCTCACAGGGCCOGATACTTC (SEQ ID NO: 23)<br>R: TCCTTTCGAGCTCAGTGCACCACAAAAC (SEQ ID NO: 24) | 55 | 33 | 242 |
| β-actin | F: CAACCGCGAGAAGATGAC (SEQ ID NO: 25)<br>R: AGGAAGGCTGGAAGAGTG (SEQ ID NO: 26) | 60 | 25 | 455 |

(4) Alkaline Phosphatase Staining and Immunohistochemistry

Alkaline phosphatase staining was carried out using Leukocyte Alkaline Phosphatase kits (Sigma). For immunocytochemistry, cells were fixed with PBS containing 4% paraformaldehyde at 4° C. for 30 minutes. Regarding nuclear-localized molecules, samples were treated with 0.2% Triton X-100 at room temperature for 15 minutes. The cells were washed three times with PBS containing 2% FBS and then incubated overnight together with primary antibodies at 4° C. in PBS containing 2% FBS. The primary antibodies include SSEA4 (1:500, Millipore), TRA-160 (1:500, Millipore), Nanog (1:1000, R&D Systems), and Oct3/4 (1:500, Santa-Cruz). As secondary antibodies, goat anti-mouse IgG coupled with Alexa Fluor 488 (1:1000, Invitrogen) and donkey anti-goat IgG coupled with Alexa Fluor 488 (1:1000, Invitrogen) were used. For staining of differentiation markers, Sox17 (1:200, R&D Systems), Foxa2 (1:200, R&D Systems), and Brachyury (1:200, R&D Systems) were used. Nuclei were stained with 1 μg/mL Hoechst 33258 (Invitrogen).

(5) RNA isolation and PCR

A Sepazol Super G reagent (Nacalai Tesque, Japan) was used to purify total RNA. Total RNA (1 microgram) was subjected to a reverse transcription reaction using SuperscriptIII (Invitrogen) and random primers (Invitrogen) according to the manufacturer's instructions. RT-PCR was performed using QuickTaq (trademark) (TOYOBO, Japan) in the manner described in H. Sakurai et al., Stem Cells, 24, 575 (2006). Table 1 lists primer sequences and amplification conditions.

Quantitative PCR (qPCR) was performed using THUNDERBIRD (trademark) qPCR mix (TOYOBO) according to the manufacturer's instructions, followed by analysis with the use of a StepOnePlus real-time PCR system (Applied Biosystems). Data were standardized with respect to GAPDH expression. Primers used for Oct3/4, Sox2, Klf4, and c-Myc were designed to detect expression of endogenous genes other than transgenes. Table 2 lists primer sequences used for qPCR.

TABLE 2

| Gene | Sequence (F: forward primer; R: reverse primer) | Amplification product size (bp) |
|---|---|---|
| GAPDH | F: ATGGAAATCCCATCACCATCTT (SEQ ID NO: 27)<br>R: CGCCCCACTTGATTTTGG (SEQ ID NO: 28) | 57 |

TABLE 2-continued

| Gene | Sequence (F: forward primer; R: reverse primer) | Amplification product size (bp) |
|---|---|---|
| Brachyury | F: ACAAAGAGATGATGGAGGAACCCG (SEQ ID NO: 29) R: AGGATGAGGATTTGCAGGTGGACA (SEQ ID NO: 30) | 110 |
| Mesogenin | F: AAGCCAGCGAGAGGGAGAAG (SEQ ID NO: 31) R: GAGGGTGTGCAGGGCATCT (SEQ ID NO: 32) | 59 |
| Mesp1 | F: CTGCCTGAGGAGCCCAAGT (SEQ ID NO: 33) R: AAAAAGCCTCGGTGCTCACA (SEQ ID NO: 34) | 64 |
| Foxa2 | F: AAAAGCCTCCGGTTTCCACTA (SEQ ID NO: 35) R: TCAGAATCTGCAGGTGCTTGA (SEQ ID NO: 36) | 62 |
| Sox17 | F: CCAGAGGCTTTTTGGATGTTTT (SEQ ID NO: 37) R: AGGTAAACTGAATGTCGAGGAGTGT (SEQ ID NO: 38) | 70 |
| Gsc | F: AGAGGAAGGTAAAAGCGATTTGG (SEQ ID NO: 39) R: GAGTTAGGTAAGTAATACGGGCAAGTG (SEQ ID NO: 40) | 75 |
| Sox1 | F: GCCCTGAGCCGACTGTGA (SEQ ID NO: 41) R: CCGTGAATACGATGAGTG (SEQ ID NO: 42) | 58 |
| Nestin | F: AGCCCTGACCACTCCAGTTTAG (SEQ ID NO: 43) R: CCCTCTATGGCTUTTCTTTCTCT (SEQ ID NO: 44) | 128 |
| NeuroD1 | F: AAGGTGGTGCCTTGCTATTCTAA (SEQ ID NO: 45) R: CCAAGCGCAGAGTCTCGATT (SEQ ID NO: 46) | 61 |
| Odx2 | F: AGGGGGTGGTTATTGGACTC (SEQ ID NO: 47) R: CATTCAGCCCAGAGAAGCTC (SEQ ID NO: 48) | 92 |
| Oct3/4 | F: GGAAGGAATTGGGAACACAAAGG (SEQ ID NO: 49) R: AACTTCACCTTCCCTCCAACCA (SEQ ID NO: 50) | 71 |
| Nanog | F: CCAAAGGCAAACAACCCACTT (SEQ ID NO: 51) R: CGGGACCTTGTCTTCCTTTTT (SEQ ID NO: 52). | 62 |

(6) Immunoblotting Method

Phosphorylated Smad1/5/8 was detected by the immunoblotting method described in T. Fukuda et al., J. Biol. Chem., 284, 7149 (2009) was detected. About 10 micrograms of proteins were separated by SDS-PAGE and transferred to a PVDF membrane for transcription. Phosphorylated Smad1/5/8 and total Smad1 were detected using an anti-phosphorylated Smad1 (Ser463/465)/Smad5 (Ser436/465)/Smad8 (Ser426/428) antibody (Cell Signaling Technology) and an anti-Smad1 antibody (EPITOMICS and Cell Signaling Technology). Data were standardized with respect to total Smad1 expression.

(7) Microarray Analysis

Total RNA (250 ng) extracted from iPS cell lines (F1-1, F2-1, F2-2, F4-1, and N3-1) cultured in the presence or absence of LDN-193189 was labeled with biotin, and were fragmented according to the manufacturer's protocol (3'IVT Express kit; Affymetrix). Next, samples were hybridized to GeneChip (registered trademark) Human Genome U133 plus 2.0 Arrays (Affymetrix). The arrays were scanned using a GeneChip (registered trademark) scanner 300 (Affymetrix). Data were analyzed by the GeneSpringGX11.5 software (Agilent technologies). Each chip was standardized with respect to the median of measured values.

(8) DNA Isolation and Nucleotide Sequencing

Mutation of the ALK2 gene (R206H: 617G>A and G356D: 1067G>A) in the FOP-derived iPS cell lines were confirmed by DNA nucleotide sequencing. The iPS cell lines were incubated overnight at 55° C. in lysis buffer containing 50 mM tris-HCl (pH 7.5), 20 mM EDTA (pH 8.0), 0.1 M NaCl, 1% SDS, and 0.15 mg/mL proteinase K. Genomic DNA was extracted using phenol/chloroform/isoamyl alcohol. Then, PCR was performed to amplify 100 ng genomic DNA. Nucleotide sequencing of the obtained PCR products was carried out using an ABI PRISM (trademark) 310 Genetic Analyzer (BigDye (registered trademark) terminator v1.1 Cycle Sequencing Kits, Applied Biosystems). Table 3 lists primer sequences used for nucleotide sequencing.

TABLE 3

| Gene | Sequence |
|---|---|
| ALK2_exon 9 (R206H)-5' | CCACGTGTCCCGGATTGCTG (SEQ ID NO: 53) |
| ALK2_exon 9 (R206H)-3' | CCAATACCTATGGTAAGGAG (SEQ ID NO: 54) |
| ALK2_exon 12 (O356D)-5' | CCCTTTTCTGCTCTCACCCCGGA (SEQ ID NO: 55) |
| ALK2_exon 12 (O356D)-3' | CACCATCCGCCTGGCCACTT (SEQ ID NO: 56) |

(9) Inhibitory Assay on Cells Upon BMP Signal Transduction

Luciferase reporter assay was carried out to evaluate ALK2 inhibitory activity of compounds in the manner described in Y. Katsuno et al., Oncogene, 27, 6322 (2008). The MDA-D-BREFluc/Rluc cell line is an MDA-231-D human breast cancer cell line which was transduced with a lentivirus capable of expressing Flue (firefly luciferase) under the control of a BMP-responsive BRE reporter and constitutively expressing Rluc (Renilla luciferase) having activity in the same manner. The MDA-D-BREFluc/Rluc cell line was co-cultured with the compounds in the presence of BMP-4 or BMP-6. After 24-hour culture, luciferase activity (for firefly and Renilla) was measured. Relative ALK2 activity was expressed as Fluc/Rluc. The half-maximal inhibitory concentration (IC50) of each compound was calculated based on the dose response curve for the compound.

(B) Results

As described above, it was attempted to generate iPS cells from skin-derived fibroblasts of four FOP patients and three healthy volunteers by the Sendai virus (SeV) method. Table 4 below shows information on patients and healthy volunteers.

TABLE 4

Patient and Healthy volunteer

| No. | Age | Gender | Diagnosis | Mutation |
|-----|-----|--------|-----------|----------|
| F1 | 18 | Male | FOP | R206H |
| F2 | 59 | Female | FOP | R206H |
| F3 | 22 | Male | FOP | R206H |
| F4 | 66 | Male | FOP | G356D |
| N1 | 48 | Male | Healthy | — |
| N2 | 54 | Male | Healthy | — |
| N3 | 48 | Male | Healthy | — |

Figure 5:
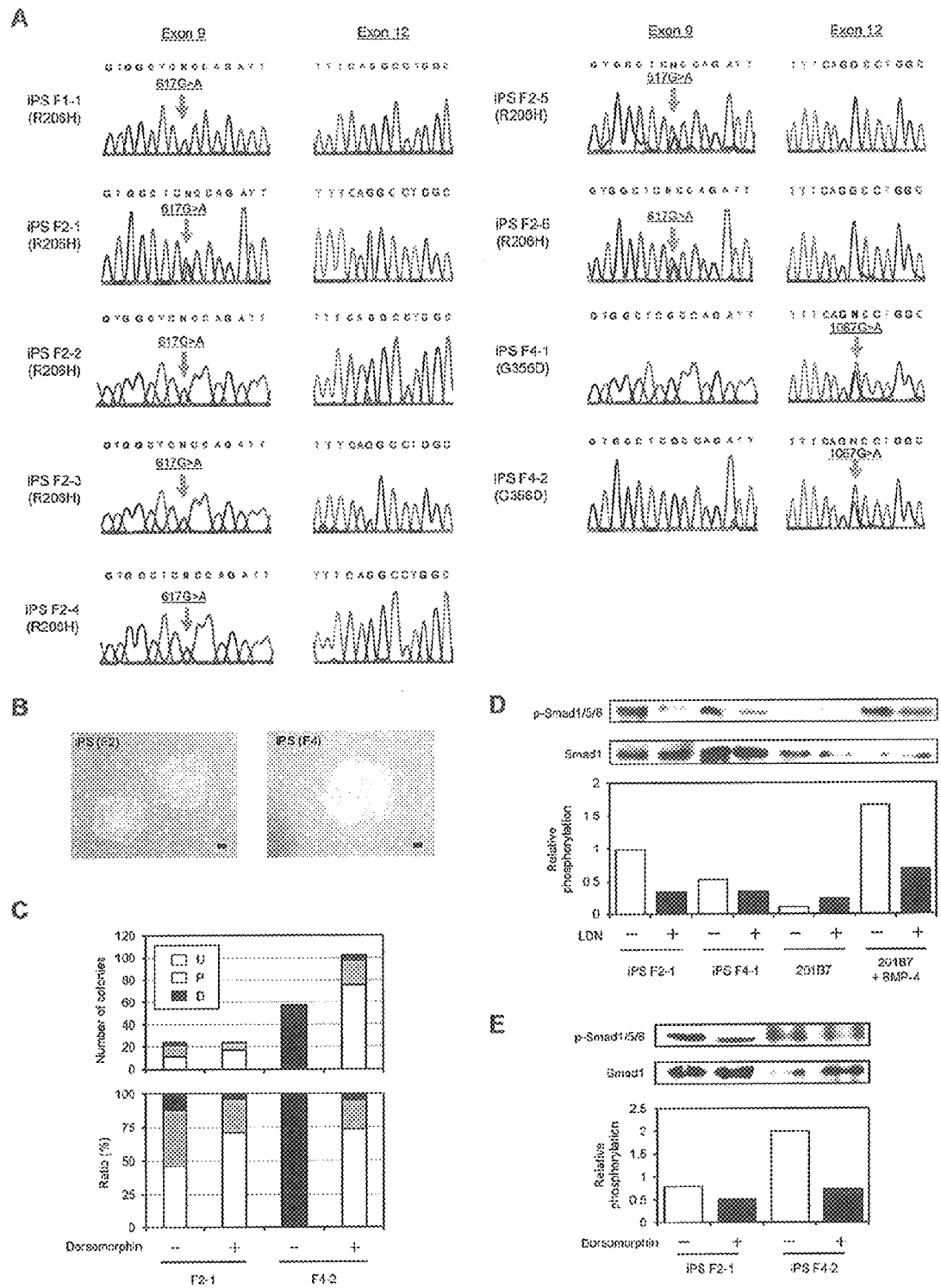
FIG. 5 show the results of examining mutation of the ALK2 gene and inhibition of ALK2 activity in FOP-iPS cells.

Three patients (F1-F3) were found to have a general mutation (R206H) of ALK2 and the other patient was found to have a rare mutation (G356D) (FIG. 5A). The frequency of formation of iPS cell colonies from FOP fibroblasts was significantly lower than that for the normal controls (FIGS. 1A and 1B). Typical colonies were mainly observed in the control culture (FIG. 1C: upper left panel). Some typical colonies were detected in the FOP-derived culture (FIG. 1C: lower left panel). Atypical colonies, which were characterized in that AP-positive morphology was observed at the center of colonies (FIG. 1C: upper right panel) or around colonies (FIG. 1C: lower right panel), were detected. The results showed that almost all of the formed colonies exhibited atypical morphology compared with the normal controls (FIGS. 1C and 1D). Isolated colonies showed flat morphology and quickly disappeared. Thus, it was impossible to continuously culture the colonies through subculture of several generations.

It is known that mutated ALK2 has constitutively active morphology that causes dysfunction of BMP signal transduction in the case of FOP (T. Fukuda et al., J Biol Chem 284, 7149 (2009); J. L. Fiori, P. C. billings, L. S. de in Pena, F. S. Kaplan, E. M. Shore, J Bone Miner Res 21, 902 (2006); E. M. Shore et al., Nat Genet 38, 525 (2006)). In this Example, the effects of ALK2 inhibitors upon formation and maintenance of iPS cells were examined. As a result of treatment with LDN-193189 (LDN) (P. B. Yu et al., Nat Med 14, 1363 (2008)) as an ALK2 inhibitor, recovery of iPS cell colony formation was observed in a dose-dependent manner (FIG. 2A). Dorsomorphin (G D. Cuny et al., Bioorg Med Chem Lett 18, 4388 (2008)) as a different ALK2 inhibitor was also able to improve the efficiency of colony formation; however, the degree of improvement was lower than that confirmed for LDN. LDN treatment was also found to have improved iPS cell generation from F4 (G356D) fibroblasts; however, the efficiency was significantly lower than that confirmed for iPS cell generation from F2 (R206H) fibroblasts (FIG. 2A).

Similarly, as the inhibitors can prevent spontaneous differentiation of iPS cells, iPS cells can be continuously maintained without differentiating in the presence of the inhibitors. Colonies formed in the presence of LDN and dorsomorphin showed typical morphology (FIGS. 2B and 5B). Further, each colony was collected and continuously maintained in the presence of LDN. As a result of amplification by nested PCR, DNA fragments of SeV were not detected (FIG. 2C). This result indicates that SeV was completely removed from every FOP-derived iPS cell line. Furthermore, analysis was conducted by RT-PCR and immunostaining. Accordingly, it was revealed that FOP-derived iPS cell lines express a series of pluripotency markers (FIGS. 2C and 2D). However, the removal of the inhibitors from culture fluid caused disruption of colony formation and thus cells immediately started to differentiate even under the maintenance conditions (FIG. 2E and FIG. 5C). The results of immunoblot analysis of phosphorylated Smad1/5/8 (i.e., an ALK2 downstream molecule) showed that ALK2 kinase activity in FOP-derived iPS cells is higher than that in normal iPS cells (FIG. 5D). Inhibition of ALK2 kinase activity was confirmed through dephosphorylation of Smad (FIGS. 5D and E).

Next, the types of cells which is obtained by spontaneously differentiation from FOP-derived iPS cells were examined. A series of differentiation markers were expressed in FOP-iPS cells cultured in the absence of ALK2 inhibitors and the expression levels were increased, compared with the control culture (FIGS. 2F and 2G). The markers showing the increased expression levels include mesodermal markers such as Brachyury and Mesp1 and endodermal markers such as Sox17 and Foxa2 (S. Tada et al., Development 132, 4363 (2005); H. Sakurai et al., Stem Cells 24, 575 (2006)). Cdx2, which is a trophectodermal marker, was also found to be upregulated in FOP-derived iPS cell lines cultured in the absence of LDN (H. Niwa et al. Cell 123, 917 (2005)). Meanwhile, the expression levels of neuroectodermal markers such as Nestin did not vary even in the absence of the inhibitors (FIG. 2G) (Y. Takashima et al., Cell 129, 1377 (2007)). The iPS cells cultured in the absence of LDN expressed pluripotency markers such as Oct3/4 (H. Niwa, J. Miyazaki, A. G Smith, Nat Genet 24, 372 (2000)) and Nanog (K. Mitsui et al., Cell 113, 631 (2003); I. Chambers et al., Cell 113, 643 (2003)) at levels lower than those of the iPS cells cultured in the presence of LDN (FIG. 2G). Marker expression patterns showed that FOP-derived iPS cells tend to spontaneously differentiate into mesoderm and endoderm other than ectoderm even if the iPS cells are cultured under the maintenance conditions.

Figure 3:
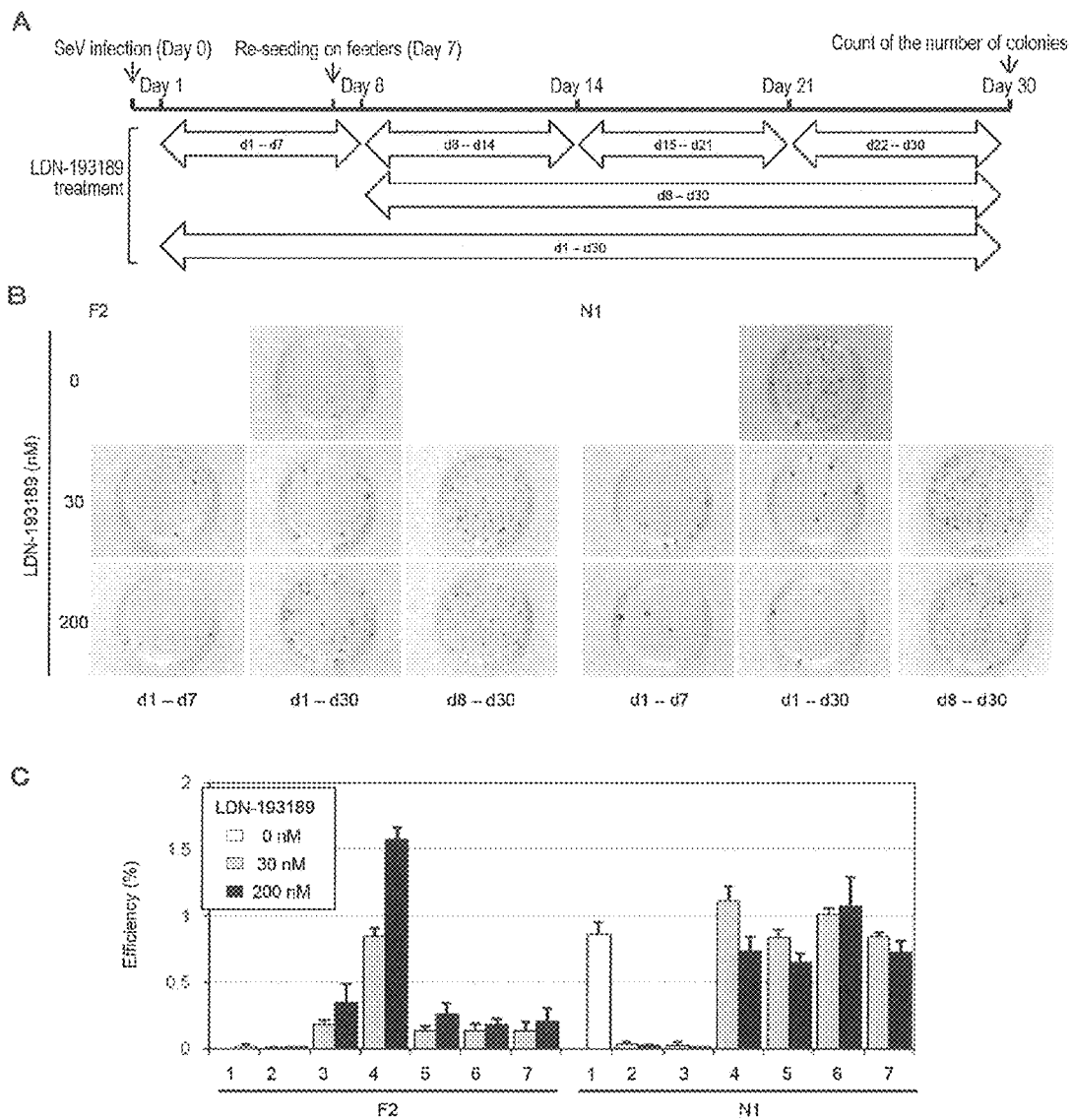
FIG. 3 show the results of examining the relationship between efficiency of formation of iPS cells from FOP-derived fibroblasts cells and the period of ALK2 inhibition.

In order to further examine effects of constitutive activation of ALK2 kinase upon formation of iPS cells, it was determined when an ALK2 mutant could inhibit formation of iPS cells during induction (FIG. 3A). When inhibitor treatment was carried out during days 8-30, the largest number of AP$^+$ colonies were detected (FIGS. 3B and 3C). The results of treatment during days 1-30 showed lower levels of efficiency than the results of treatment during days 8-30. In addition, efficiency of colony formation did not recover through treatment only during days 1-7 (FIGS. 3B and 3C). Next, the period of days 8-30 was divided to three periods, i.e., a period of days 8-14, a period of days 15-21, and a period of 22-30, and the number of iPS colonies was counted for each period. Unexpectedly, only few iPS cell colonies were detected during each period (FIG. 3C). These results suggest that mutated ALK2 kinase inhibition is required not in the initial period of induction of iPS cells (days 1-7) but in the other period (days 8-30) for formation of FOP-derived iPS cells.

Figure 6:
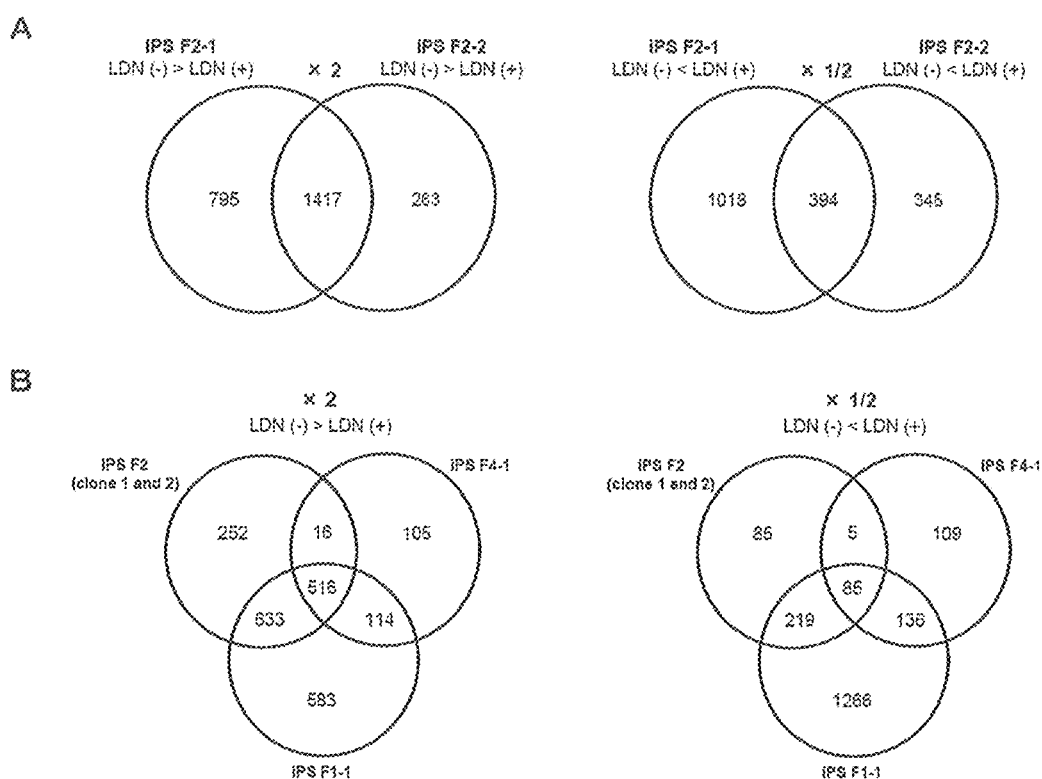
FIG. 6 show the results of analyzing gene expression in FOP-iPS cells.

The results of DNA microarray analysis show that general gene expression patterns in LDN-treated FOP-derived iPS cells differ from those in FOP-derived iPS cells treated in the absence of LDN (FIG. 4A). Of 54,675 analyzed genes, there were more than twofold differences in terms of the expression levels of 1,417 genes between iPS cell clones treated in the absence of LDN and LDN-treated iPS cell clones (FIGS. 6A and B). It was confirmed that the expression levels of mesodermal and endodermal markers in iPS cells treated in the absence of LDN were greater than those in LDN-treated iPS cells, which did not apply to neuroectodermal markers such as Nestin and Sox1 (Y. Takashima et al., Cell 129, 1377 (2007)) (FIG. 4A). Meanwhile, LDN treatment did not influence the expression of differentiation markers in normal iPS cell lines (FIG. 4A).

Treatment with ALK2 kinase inhibitors allowed iPS cells to generate from FOP fibroblasts so as to be maintained with pluripotency. This result suggests that screening of ALK2 inhibitor candidates can be carried out according to the method of the present invention.

In this Example, it was demonstrated that constitutive activation of ALK2 inhibits formation and maintenance of human iPS cells. ALK2 mutation that causes kinase activity to show constitutive morphology is always observed in FOP, suggesting that ALK2 mutation would cause the disease (T. Fukuda et al, J Biol Chem 284, 7149 (2009); P. C. Billings et al., J bone Miner Res 23, 305 (2008); J. L. Fiori, P. C. Billings, L. S. de la Pena, F. S. Kaplan, E. M. Shore, J Bone Miner Res 21, 902 (2006); F. S. Kaplan et al., Hum Mutat 30, 379 (2009), A. B. Shafritz et al., N Engl J Med 335, 555 (1996); Q. Shen et al., J Clin Invest 119, 3462 (2009); E. M. Shore et al., Nat Genet 38, 525 (2006)). In this Example, it was shown that constitutive activation of BMP signals inhibits formation of iPS cells during reprogramming except for the initial phase of reprogramming. It was shown that inhibition of BMP signal transduction suppresses generation of iPS cells from normal controls during the initial period (days 1-7). Therefore, the role of BMP signals in the control of reprogramming has mutually related two aspects; one aspect is to stimulate reprogramming in an early phase, and the other aspect is to suppress reprogramming in a later phase.

Hitherto, several studies reported not only that iPS cells established from patients can reproduce some aspects of morphology of a disease, but also that the cells can be used for better design to obtain expected performance of advanced medical care (J. T. Dimos et al., Science 321, 1218 (2008); A. D. Ebert et al., Nature 457, 277 (2009); G H. Liu et al., Nature 472, 221 (2011); M. C. Marchetto et al., Cell 143, 527 (2010); F. Soldner et al., Cell 136, 964 (2009)). In this Example, it was demonstrated that causes of diseases and the subsequent phenomena induced by the diseases in cells inhibit formation of iPS cells and therefore the removal of the causes can improve efficiency of formation of iPS cell colonies. Thus, elucidation of the reasons for unsuccessful production of disease-derived iPS cells leads to the discovery of clues to causes or pathogenetic phenomena of diseases.

In this Example, it was revealed that new candidates for promising therapeutic methods can be found based on the fact that it is impossible to generate and maintain FOP-derived iPS cells. The system used herein might not always be associated with symptoms of FOP. However, it was possible for known ALK2 inhibitors to improve efficiency of formation and maintenance of FOP-derived iPS cells. It is the first step to search for new compounds that can serve as ALK2 inhibitors in order to develop new drugs for reliable therapeutic methods for FOP. In this regard, the patient-derived cell models presented herein contribute to the discovery of new compounds for FOP treatment. The method of the present invention can be used as means not only for understanding the mechanism of a disease but also for finding new compound candidates for promising therapeutic methods.

Example 2

In this Example, sodium butyrate (NaB) was used to induce iPS cells from fibroblasts of infantile Krabbe disease patients.

Figure 7:
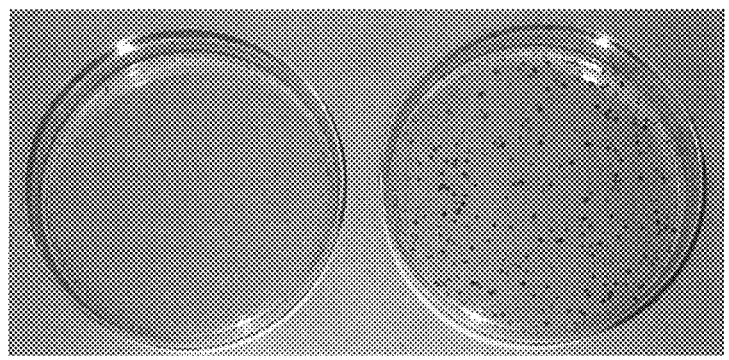
FIG. 7 shows the results of inducing iPS cells from fibroblasts derived from infantile Krabbe disease patients.

As in the case of Example 1, fibroblasts were prepared from skin samples of infantile Krabbe disease patients and were seeded on a 6-well plate ($5 \times 10^5$ cells/well) on the day before Sendai virus (SeV) infection. The fibroblasts were infected with SeV capable of expressing Oct-3/4, Sox2, Klf4, and cMyc. On the next day of infection, medium (DMEM+10% FBS+500 uM sodium butyrate) was renewed, and the medium was renewed on each of the following days. The fibroblasts were recovered on day 7 after viral infection and $3.5 \times 10^5$ cells were seeded on mitomycin-treated mouse embryonic fibroblasts (MMC-MEF). On the next day of seeding, the cells were divided into the following groups: a test group of human embryonic stem cell (hES cell) culture medium [DMEM/F12+20% Knockout serum replacement (KSR)+2 mM L-glutamate+100 mM non-essential amino acid+100 mM 2-mercaptoethanol+a 5 ng/mL basic fibroblast growth factor (bFGF)] supplemented with 500 μM sodium butyrate (NaB); and a supplement-free medium group, i.e., a group of the same hES cell culture medium free from NaB. Each medium was renewed every two days until day 12 after infection. The medium was replaced by hES culture medium free from 500 uM sodium butyrate on day 13 after infection. Thereafter, each medium was renewed every day. On day 28 after infection, as shown in Example 1, iPS cell colonies were stained by alkaline phosphatase staining, the number of colonies was counted, and the efficiency of iPS cell induction was determined. FIG. 7 shows the results.

As shown in FIG. 7, the rate of iPS cell induction efficiency was 0% for the fibroblasts of Krabbe disease patients in the case of the usual iPS cell induction medium free from sodium butyrate. Meanwhile, iPS cell induction efficiency was improved (0.16%) in the case of the iPS cell induction medium supplemented with 500 μM sodium butyrate (NaB). That is, it was demonstrated in this Example that, according to the present invention, it is possible to select a substance capable of inducing iPS cells with the use of Krabbe disease patient-derived cells from which it is difficult to produce iPS cells. It was also demonstrated that, according to the present invention, it is possible to produce iPS cells from Krabbe disease patient-derived cells from which it is difficult to produce iPS cells.

The invention claimed is:

1. A method for screening a substance, which comprises:
culturing fibroblast cells derived from an individual affected by fibrodysplasia ossificans progressiva, the cells being transfected with reprogramming genes, in the presence of test substances to generate induced pluripotent stem cells; and
selecting a test substance capable of promoting induction of induced pluripotent stem cells from the fibroblast cells.

2. The method according to claim 1, wherein the fibrodysplasia ossificans progressiva is caused by a change in activity of activin receptor-like kinase 2.

3. The method according to claim 1, wherein the fibroblast cells are human cells.

4. The method according to claim 3, wherein the fibroblast cells contain a gene encoding an amino acid sequence derived from the amino acid sequence shown in SEQ ID NO: 2 by substitution of arginine at position 206 with histidine.

5. The method according to claim 3, wherein the fibroblast cells contain a gene encoding an amino acid sequence derived from the amino acid sequence shown in SEQ ID NO: 2 by substitution of glycine at position 356 with aspartic acid.

6. The method according to claim 1, wherein the reprogramming genes are an Oct3/4 gene, Klf4 gene, Sox2 gene, and c-Myc gene.

7. The method according to claim 1, which further comprises selecting a test substance capable of inhibiting activin receptor-like kinase 2.

8. The method according to claim 1, which is a method for screening a therapeutic agent of fibrodysplasia ossificans progressiva.

* * * * *

SEQUENCE LISTING

```
<160> NUMBER OF SEQ ID NOS: 60

<210> SEQ ID NO 1
<211> LENGTH: 1530
<212> TYPE: DNA
<213> ORGANISM: Homo sapiens
<220> FEATURE:
<221> NAME/KEY: CDS
<222> LOCATION: (1)..(1527)
```

<400> SEQUENCE: 1

```
atg gta gat gga gtg atg att ctt cct gtg ctt atc atg att gct ctc      48
Met Val Asp Gly Val Met Ile Leu Pro Val Leu Ile Met Ile Ala Leu
1               5                   10                  15 ccc tcc cct agt atg gaa gat gag aag ccc aag gtc aac ccc aaa ctc      96
Pro Ser Pro Ser Met Glu Asp Glu Lys Pro Lys Val Asn Pro Lys Leu
            20                  25                  30 tac atg tgt gtg tgt gaa ggt ctc tcc tgc ggt aat gag gac cac tgt     144
Tyr Met Cys Val Cys Glu Gly Leu Ser Cys Gly Asn Glu Asp His Cys
        35                  40                  45 gaa ggc cag cag tgc ttt tcc tca ctg agc atc aac gat ggc ttc cac     192
Glu Gly Gln Gln Cys Phe Ser Ser Leu Ser Ile Asn Asp Gly Phe His
    50                  55                  60 gtc tac cag aaa ggc tgc ttc cag gtt tat gag cag gga aag atg acc     240
Val Tyr Gln Lys Gly Cys Phe Gln Val Tyr Glu Gln Gly Lys Met Thr
65                  70                  75                  80 tgt aag acc ccg ccg tcc cct ggc caa gcc gtg gag tgc tgc caa ggg     288
Cys Lys Thr Pro Pro Ser Pro Gly Gln Ala Val Glu Cys Cys Gln Gly
                85                  90                  95 gac tgg tgt aac agg aac atc acg gcc cag ctg ccc act aaa gga aaa     336
Asp Trp Cys Asn Arg Asn Ile Thr Ala Gln Leu Pro Thr Lys Gly Lys
            100                 105                 110 tcc ttc cct gga aca cag aat ttc cac ttg gag gtt ggc ctc att att     384
Ser Phe Pro Gly Thr Gln Asn Phe His Leu Glu Val Gly Leu Ile Ile
        115                 120                 125 ctc tct gta gtg ttc gca gta tgt ctt tta gcc tgc ctg ctg gga gtt     432
Leu Ser Val Val Phe Ala Val Cys Leu Leu Ala Cys Leu Leu Gly Val
    130                 135                 140 gct ctc cga aaa ttt aaa agg cgc aac caa gaa cgc ctc aat ccc cga     480
Ala Leu Arg Lys Phe Lys Arg Arg Asn Gln Glu Arg Leu Asn Pro Arg
145                 150                 155                 160 gac gtg gag tat ggc act atc gaa ggg ctc atc acc acc aat gtt gga     528
Asp Val Glu Tyr Gly Thr Ile Glu Gly Leu Ile Thr Thr Asn Val Gly
                165                 170                 175 gac agc act tta gca gat tta ttg gat cat tcg tgt aca tca gga agt     576
Asp Ser Thr Leu Ala Asp Leu Leu Asp His Ser Cys Thr Ser Gly Ser
            180                 185                 190 ggc tct ggt ctt cct ttt ctg gta caa aga aca gtg gct cgc cag att     624
Gly Ser Gly Leu Pro Phe Leu Val Gln Arg Thr Val Ala Arg Gln Ile
        195                 200                 205 aca ctg ttg gag tgt gtc ggg aaa ggc agg tat ggt gag gtg tgg agg     672
Thr Leu Leu Glu Cys Val Gly Lys Gly Arg Tyr Gly Glu Val Trp Arg
    210                 215                 220 ggc agc tgg caa ggg gag aat gtt gcc gtg aag atc ttc tcc tcc cgt     720
Gly Ser Trp Gln Gly Glu Asn Val Ala Val Lys Ile Phe Ser Ser Arg
225                 230                 235                 240 gat gag aag tca tgg ttc agg gaa acg gaa ttg tac aac act gtg atg     768
Asp Glu Lys Ser Trp Phe Arg Glu Thr Glu Leu Tyr Asn Thr Val Met
                245                 250                 255 ctg agg cat gaa aat atc tta ggt ttc att gct tca gac atg aca tca     816
Leu Arg His Glu Asn Ile Leu Gly Phe Ile Ala Ser Asp Met Thr Ser
            260                 265                 270 aga cac tcc agt acc cag ctg tgg tta att aca cat tat cat gaa atg     864
Arg His Ser Ser Thr Gln Leu Trp Leu Ile Thr His Tyr His Glu Met
        275                 280                 285 gga tcg ttg tac gac tat ctt cag ctt act act ctg gat aca gtt agc     912
Gly Ser Leu Tyr Asp Tyr Leu Gln Leu Thr Thr Leu Asp Thr Val Ser
    290                 295                 300
```

-continued

```
tgc ctt cga ata gtg ctg tcc ata gct agt ggt ctt gca cat ttg cac      960
Cys Leu Arg Ile Val Leu Ser Ile Ala Ser Gly Leu Ala His Leu His
305             310                 315                 320 ata gag ata ttt ggg acc caa ggg aaa cca gcc att gcc cat cga gat     1008
Ile Glu Ile Phe Gly Thr Gln Gly Lys Pro Ala Ile Ala His Arg Asp
            325                 330                 335 tta aag agc aaa aat att ctg gtt aag aag aat gga cag tgt tgc ata     1056
Leu Lys Ser Lys Asn Ile Leu Val Lys Lys Asn Gly Gln Cys Cys Ile
        340                 345                 350 gca gat ttg ggc ctg gca gtc atg cat tcc cag agc acc aat cag ctt     1104
Ala Asp Leu Gly Leu Ala Val Met His Ser Gln Ser Thr Asn Gln Leu
    355                 360                 365 gat gtg ggg aac aat ccc cgt gtg ggc acc aag cgc tac atg gcc ccc     1152
Asp Val Gly Asn Asn Pro Arg Val Gly Thr Lys Arg Tyr Met Ala Pro
370                 375                 380 gaa gtt cta gat gaa acc atc cag gtg gat tgt ttc gat tct tat aaa     1200
Glu Val Leu Asp Glu Thr Ile Gln Val Asp Cys Phe Asp Ser Tyr Lys
385                 390                 395                 400 agg gtc gat att tgg gcc ttt gga ctt gtt ttg tgg gaa gtg gcc agg     1248
Arg Val Asp Ile Trp Ala Phe Gly Leu Val Leu Trp Glu Val Ala Arg
            405                 410                 415 cgg atg gtg agc aat ggt ata gtg gag gat tac aag cca ccg ttc tac     1296
Arg Met Val Ser Asn Gly Ile Val Glu Asp Tyr Lys Pro Pro Phe Tyr
        420                 425                 430 gat gtg gtt ccc aat gac cca agt ttt gaa gat atg agg aag gta gtc     1344
Asp Val Val Pro Asn Asp Pro Ser Phe Glu Asp Met Arg Lys Val Val
    435                 440                 445 tgt gtg gat caa caa agg cca aac ata ccc aac aga tgg ttc tca gac     1392
Cys Val Asp Gln Gln Arg Pro Asn Ile Pro Asn Arg Trp Phe Ser Asp
450                 455                 460 ccg aca tta acc tct ctg gcc aag cta atg aaa gaa tgc tgg tat caa     1440
Pro Thr Leu Thr Ser Leu Ala Lys Leu Met Lys Glu Cys Trp Tyr Gln
465                 470                 475                 480 aat cca tcc gca aga ctc aca gca ctg cgt atc aaa aag act ttg acc     1488
Asn Pro Ser Ala Arg Leu Thr Ala Leu Arg Ile Lys Lys Thr Leu Thr
            485                 490                 495 aaa att gat aat tcc ctc gac aaa ttg aaa act gac tgt tga             1530
Lys Ile Asp Asn Ser Leu Asp Lys Leu Lys Thr Asp Cys
        500                 505
```

<210> SEQ ID NO 2
<211> LENGTH: 509
<212> TYPE: PRT
<213> ORGANISM: Homo sapiens

<400> SEQUENCE: 2

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
            85                  90                  95

Asp Trp Cys Asn Arg Asn Ile Thr Ala Gln Leu Pro Thr Lys Gly Lys
```

```
                100             105              110
Ser Phe Pro Gly Thr Gln Asn Phe His Leu Glu Val Gly Leu Ile Ile
            115                 120             125

Leu Ser Val Val Phe Ala Val Cys Leu Leu Ala Cys Leu Leu Gly Val
130             135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
            195                 200                 205

Thr Leu Leu Glu Cys Val Gly Lys Gly Arg Tyr Gly Glu Val Trp Arg
            210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
            290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
            370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

<210> SEQ ID NO 3

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcactag gtgatatcga gc                                              22

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accagacaag agtttaagag atatgtatc                                       29

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgagccata tgacagctcg                                                 20

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagatatgta tccttttaaa ttttcttgtc ttcttg                               36

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacaggggga ggggaggagc tagg                                            24

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttccctcca accagttgcc ccaaac                                          26

<210> SEQ ID NO 9
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggaaatggg aggggtgcaa aagagg                                          26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgcgtgagt gtggatggga ttggtg                                          26

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gattacgcgg gctgcggcaa aacctacaca                                      30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgattgtagt gctttctggc tgggctcc                                        28

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgtcctggg aagggagatc cggagc                                          26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttgaggggca tcgtcgcggg aggctg                                          26

<210> SEQ ID NO 15
<211> LENGTH: 25
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 15
cagccccgat tcttccacca gtccc                                    25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
cggaagattc ccagtcgggt tcacc                                    25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
cttatgctac gtaaaggagc tggg                                     24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gtgccaaccc aggtcccgga agtt                                     24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
cagatcctaa acagctcgca gaat                                     24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcgtacgcaa attaaagtcc aga                                      23

<210> SEQ ID NO 21
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 21 aaacccagc acatcaactc                                                    20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtcattccct gggtggttc                                                    19

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgctgctcac agggcccgat acttc                                             25

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcctttcgag ctcagtgcac cacaaaac                                          28

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caaccgcgag aagatgac                                                     18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aggaaggctg gaagagtg                                                     18

<210> SEQ ID NO 27
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 27
atggaaatcc catcaccatc tt                                             22

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgccccactt gattttgg                                                  18

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acaaagagat gatggaggaa cccg                                           24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aggatgagga tttgcaggtg gaca                                           24

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagccagcga gagggagaag                                                20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagggtgtgc agggcatct                                                 19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 33
ctgcctgagg agcccaagt					19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaaaagcctc ggtgctcaca					20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaaagcctcc ggtttccact a					21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcagaatctg caggtgcttg a					21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccagaggctt tttggatgtt tt				22

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aggtaaactg aatgtcgagg agtgt				25

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agaggaaggt aaaagcgatt tgg                                                  23

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 40
gagttaggta agtaatacgg gcaagtg                                              27

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 41
gccctgagcc gactgtga                                                        18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 42
ccgtgaatac gatgagtg                                                        18

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 43
agccctgacc actccagttt ag                                                   22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 44
ccctctatgg ctgtttctttt ctct                                                24

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

```
<400> SEQUENCE: 45
aaggtggtgc cttgctattc taa                                           23

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaagcgcag agtctcgatt                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agggggtggt tattggactc                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cattcagccc agagaagctc                                               20

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggaaggaatt gggaacacaa agg                                           23

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aacttcacct tccctccaac ca                                            22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```
ccaaaggcaa acaacccact t                                    21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgggaccttg tcttcctttt t                                    21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccacgtgtcc cggattgctg                                      20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccaataccta tggtaaggag                                      20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cccttttctg ctctcacccc gga                                  23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caccatccgc ctggccactt                                      20

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)

```
<223> OTHER INFORMATION: a, c, t, g, unknown or other

<400> SEQUENCE: 57
gtggctcncc agatt                                                    15

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tttcaggcct ggc                                                      13

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gtggctcgcc agatt                                                    15

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 60
tttcagncct ggc                                                      13
```